(12) United States Patent
Meadows et al.

(10) Patent No.: US 12,365,905 B2
(45) Date of Patent: Jul. 22, 2025

(54) HOST CELLS AND METHODS FOR REDUCING ISOPRENOID PRECURSORS AND ISOPRENOIDS BY GERANYLGERANYL REDUCTASE

(71) Applicant: The Regents of the University of California, Oakland, CA (US)

(72) Inventors: Corey Meadows, Berkeley, CA (US); Brett Garabedian, Basel (CH); Florence Mingardon, Oakland, CA (US); Angelique Chanal, Puteaux (FR); Taek Soon Lee, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/725,810

(22) Filed: Dec. 23, 2019

(65) Prior Publication Data

US 2020/0255841 A1 Aug. 13, 2020

Related U.S. Application Data

(60) Provisional application No. 62/784,088, filed on Dec. 21, 2018.

(51) Int. Cl.
*C12N 15/52* (2006.01)
*C12P 5/00* (2006.01)

(52) U.S. Cl.
CPC ............ *C12N 15/52* (2013.01); *C12P 5/007* (2013.01); *C12Y 103/01083* (2013.01)

(58) Field of Classification Search
CPC ......... C12N 15/52; C12N 9/001; C12P 5/007; C12P 7/04; C12Y 103/01083
See application file for complete search history.

(56) References Cited

U.S. PATENT DOCUMENTS

| 8,709,767 B2 | 4/2014 | Maurer et al. | |
| 2003/0125573 A1* | 7/2003 | Millis | C12N 9/1085 |
| | | | 549/411 |

FOREIGN PATENT DOCUMENTS

WO WO-2014100726 A2 * 6/2014 ............ C07C 11/18

OTHER PUBLICATIONS

Whisstock et al. Quaterly Reviews of Biophysics, "Prediction of protein function from protein sequence and structure", (2003), 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Sasaki et al. Structure and mutations analysis of Archaeal geranylgeranyl reductase. J. Mol. Biol. (2011), 409: 543-557.*
Addlesee HA, Hunter CN: Physical mapping and functional assignment of the geranylgeranyl-bacteriochlorophyll reductase gene, bchP, of Rhodobacter sphaeroides. J Bacteriol 1999, 181(23):7248-7255.
Ajikumar PK, Xiao WH, Tyo KEJ, Wang Y, Simeon F, Leonard E, Mucha O, Phon TH, Pfeifer B, Stephanopoulos G: soprenoid Pathway Optimization for Taxol Precursor Overproduction in *Escherichia coli*. Science 2010, 330 (6000): 70-74.
Bohlmann J, Meyer-Gauen G, Croteau R: Plant terpenoid synthases: Molecular biology and phylogenetic analysis. Proc Natl Acad Sci U S A 1998, 95(8):4126-4133.
Dickschat JS: Bacterial terpene cyclases. Nat Prod Rep 2016, 33(1):87-110.
Eichler J, Guan ZQ: Lipid sugar carriers at the extremes: The phosphodolichols Archaea use in N-glycosylation. Biochim Biophys Acta Mol Cell Biol Lipids 2017, 1862(6):589-599.
Goldstein JL, Brown MS: Regulation of the mevalonate pathway. Nature 1990, 343(6257):425-430.
Hemmi H, Takahashi Y, Shibuya K, Nakayama T, Nishino T: Menaquinone-specific prenyl reductase from the hyperthermophilic archaeon Archaeoglobus fulgidus. J Bacteriol 2005, 187(6):1937-1944.
Isobe K, Ogawa T, Hirose K, Yokoi T, Yoshimura T, Hemmi H: Geranylgeranyl Reductase and Ferredoxin from Methanosarcina acetivorans Are Required for the Synthesis of Fully Reduced Archaeal Membrane Lipid in *Escherichia coli* Cells. J Bacteriol 2014, 196(2):417-423.
Jain S, Caforio A, Driessen AJM: Biosynthesis of archaeal membrane ether lipids. Front Microbiol 2014, 5:16.
Keller Y, Bouvier F, D'Harlingue A, Camara B: Metabolic compartmentation of plastid prenyllipid biosynthesis—Evidence for the involvement of a multifunctional geranylgeranyl reductase. Eur J Biochem 1998, 251(1-2):413-417.
Koga Y, Morii H: Biosynthesis of ether-type polar lipids in archaea and evolutionary considerations. Microbiol Mol Biol Rev 2007, 71(1):97-120.
Kung Y, McAndrew RP, Xie XK, Liu CC, Pereira JH, Adams PD, Keasling JD: Constructing Tailored Isoprenoid Products by Structure-Guided Modification of Geranylgeranyl Reductase. Structure 2014, 22(7):1028-1036.
Liang PH, Ko TP, Wang AHJ: Structure, mechanism and function of prenyltransferases. Eur J Biochem 2002, 269 (14): 3339-3354.
Lubben M, Morand K: Novel prenylated hemes as cofactors of cytochrome oxidases. Archaea have modified hemes A and O. J Biol Chem 1994, 269(34):21473-21479.

(Continued)

*Primary Examiner* — Iqbal H Chowdhury
(74) *Attorney, Agent, or Firm* — Robin C. Chiang; LAWRENCE BERKELEY

(57) ABSTRACT

The present invention provides for a genetically modified host cell capable of reducing one or more isoprenoid, or precursor thereof, said genetically modified host cell comprising one or more geranylgeranyl reductases (GGRs), or polypeptides comprising an amino acid sequence having at least 70% identity to an amino acid sequence of a geranylgeranyl reductase (GGR), wherein the polypeptide comprises the enzymatic activity for catalyzing one or more GGR catalyzed reactions, and/or reducing one or more $C_{15}$ or $C_{20}$ prenyl alcohols or prenyl pyrophosphates.

8 Claims, 16 Drawing Sheets

Specification includes a Sequence Listing.

(56) References Cited

OTHER PUBLICATIONS

Martin VJJ, Pitera DJ, Withers ST, Newman JD, Keasling JD: Engineering a mevalonate pathway in *Escherichia coli* for production of terpenoids. Nat Biotechnol 2003, 21(7):796-802.

Mizoguchi T, Isaji M, Yamano N, Harada J, Fujii R, Tamiaki H: Molecular Structures and Functions of Chlorophylls-a Esterified with Geranylgeranyl, Dihydrogeranylgeranyl, and Tetrahydrogeranylgeranyl Groups at the 17-Propionate Residue in a Diatom, Chaetoceros calcitrans. Biochemistry 2017, 56(28):3682-3688.

Murakami M, Shibuya K, Nakayama T, Nishino T, Yoshimura T, Hemmi H: Geranylgeranyl reductase involved in the biosynthesis of archaeal membrane lipids in the hyperthermophilic archaeon Archaeoglobus fulgidus. Febs J 2007, 274(3):805-814.

Naparstek S, Guan ZQ, Eichler J: A predicted geranylgeranyl reductase reduces the omega-position isoprene of dolichol phosphate in the halophilic archaeon, Haloferax volcanii. Biochim Biophys Acta Mol Cell Biol Lipids 2012, 1821(6):923-933.

Ogawa T, Isobe K, Mori T, Asakawa S, Yoshimura T, Hemmi H: A novel geranylgeranyl reductase from the methanogenic archaeon Methanosarcina acetivorans displays unique regiospecificity. Febs J 2014, 281(14):3165-3176.

Pazouki L, Niinemets U: Multi-Substrate Terpene Synthases: Their Occurrence and Physiological Significance. Front Plant Sci 2016, 7:16.

Rodriguez S, Kirby J, Denby CM, Keasling JD: Production and quantification of sesquiterpenes in Saccharomyces cerevisiae, including extraction, detection and quantification of terpene products and key related metabolites. Nat Protoc 2014, 9(8):1980-1996.

Rohmer M: The discovery of a mevalonate-independent pathway for isoprenoid biosynthesis in bacteria, algae and higher plants. Nat Prod Rep 1999, 16(5):565-574.

Sato S, Murakami M, Yoshimura T, Hemmi H: Specific partial reduction of geranylgeranyl diphosphate by an enzyme from the thermoacidophilic archaeon Sulfolobus acidocaldarius yields a reactive prenyl donor, not a dead-end product. J Bacteriol 2008, 190(11):3923-3929.

Zhang FL, Casey PJ: Protein prenylation: Molecular mechanisms and functional consequences. Annu Rev Biochem 1996, 65:241-269.

\* cited by examiner

A

B

HOST CELLS AND METHODS FOR REDUCING ISOPRENOID PRECURSORS AND ISOPRENOIDS BY GERANYLGERANYL REDUCTASE

CROSS-REFERENCE TO RELATED APPLICATIONS

This application claims priority to U.S. Provisional Patent Application Ser. No. 62/784,088, filed on Dec. 21, 2018, which is hereby incorporated by reference.

STATEMENT OF GOVERNMENTAL SUPPORT

This invention described and claimed herein was made utilizing funds supplied by the U.S. Department of Energy under Contract No. DE-AC02-05CH11231. The government has certain rights in this invention.

FIELD OF THE INVENTION

The present invention is in the field of reducing isoprenoid precursors and isoprenoids by geranylgeranyl reductases.

BACKGROUND OF THE INVENTION

Manufacturing of terpenoid based compounds has been studied extensively in synthetic biology. The two biosynthetic pathways for terpene monomer biosynthesis are the mevalonate and 1-deoxy-D-xylulose 5-phosphate pathways, where pyruvate is ultimately converted to either of the $C_5$ terpene building blocks, isopentenyl pyrophosphate or dimethylallyl pyrophosphate [1, 2]. These monomer units are subsequently fused by various prenyl transferases to make geranyl pyrophosphate (GPP, $C_{10}$), farnesyl pyrophosphate (FPP, $C_{15}$), and geranylgeranyl pyrophosphate (GGPP, $C_{20}$) [3]. The structural diversity of terpenes allows for a broad range of uses in areas including dietary supplements, polymer feedstocks, pharmaceuticals and cosmetics, household cleaners, and fuels [4-8]. Much of this structural diversity is achieved via downstream cyclization and redox steps on GPP, FPP, and GGPP using a plethora of terpene synthases [9-11]. Combinations of these core isoprenoid pyrophosphate intermediates serve as starting points for cholesterol biosynthesis, antibiotic biosynthesis, cofactor biosynthesis, and protein prenylation [12-16].

While microbes including *E. coli* and *S. cerevisiae* have emerged as robust hosts in the production of terpenoids, producing specially tailored natural products will require the use of novel chemistries and biosynthetic pathways. For example, isoprenoids have been considered as a promising precursor of alternative fuels, but reduction of isoprenoid double bonds are required to decrease the reactivity and sensitivity to oxidation and make them better fuels. Enzymatic alkene hydrogenation, however, is typically assisted by adjacent electron withdrawing groups as observed in examples including old yellow enzyme, fatty acid enoyl reductases, and enone reductases [17-20].

Reduction of unactivated substrates like prenyl pyrophosphates typically involves oxidoreductases from the geranylgeranyl reductase (GGR) family. GGR generates fully saturated isoprenoid intermediates in archaeal membrane biosynthesis [21, 22]. In archaea, GGR's native activity is believed to fully reduce all prenyl groups within the $C_{20}$ isoprenoid chain of 2,3-di-O-geranylgeranylglyceryl phosphate (DGGGP) before carbon-carbon bond formation of reduced $C_{20}$ isoprenoid chains form fully reduced $C_{40}$ precursors needed for membrane synthesis [23, 24]. Moreover, in various organisms such as eukaryotes, bacteria, and archaea, GGRs also have been demonstrated to reduce a variety of prenylated substrates, including chlorophyll, tocopherol, dolichol, and menaquinone [25-28]. However, very few GGRs have been confirmed as oxidoreductases, and most enzymes having prenyl reductase activity were derived from species that thrive under extremophilic conditions or utilize photosynthesis for energy transduction [25-32]. To date, only two crystal structures have been solved for GGRs from archaeal organisms. Reducing equivalents are thought to be derived from a NAD(P)H/Ferredoxin reductase, in which electron transfer is conducted throughout the protein and modulated by a conserved active site cysteine within the cofactor binding domain, located directly behind the FAD isoalloxazine ring [31].

SUMMARY OF THE INVENTION

The present invention provides for a genetically modified host cell capable of reducing one or more isoprenoid, or precursor thereof, said genetically modified host cell comprising one or more geranylgeranyl reductases (GGRs), or polypeptides comprising an amino acid sequence having at least 70% identity to an amino acid sequence of a geranylgeranyl reductase (GGR) of Table 1 of Example 1, or Table 1 of Example 2, wherein the polypeptide comprises the enzymatic activity for catalyzing one or more of the GGR catalyzed reactions depicted in FIG. 1 of Example 1, and/or Scheme 1, and/or reducing one or more $C_{15}$ or $C_{20}$ prenyl alcohols or prenyl pyrophosphates.

The present invention provides for an isolated or purified geranylgeranyl reductase (GGR) of Table 1 of Example 1, or Table 1 of Example 2.

The present invention provides for a geranylgeranyl reductase (GGR), or a polypeptide comprising an amino acid sequence having at least 70% identity to an amino acid sequence of a geranylgeranyl reductase (GGR) of Table 1 of Example 1, or Table 1 of Example 2, comprising one or more mutations in the amino acid residue which corresponds to L377, D82, Q84, D207, E209, P212, N359, K367, G298, G299, G300, A304, 5307, or G308 of *Sulfolobus acidocaldarius* GRR (SaGRR), or any other amino acid residue described herein. In some embodiments, the mutation is a substitution mutation. In some embodiments, the mutation causes the polypeptide to have an increase in enzymatic activity to reduce an isoprenoid, or precursor thereof, and/or a decrease in enzymatic activity to reduce another isoprenoid, or precursor thereof.

The present invention provides for a vector or expression vector encoding the geranylgeranyl reductase (GGR) or polypeptide of the present invention, such as in an open reading frame (ORF), operatively linked to a promoter. In some embodiments, the genetically modified host cell of the present invention comprises the vector or expression vector of the present invention, wherein the host cell is capable of expressing the geranylgeranyl reductase (GGR) or polypeptide. In some embodiments, the GGR or polypeptide is heterologous to the host cell. In some embodiments, the GGR or polypeptide is heterologous to the vector, expression vector, and/or promoter.

In some embodiments, the isoprenoid, or precursor thereof, is geranyl pyrophosphate (GPP), farnesyl pyrophosphate (FPP), geranylgeranyl pyrophosphate (GGPP), geranylgeraniol, farnesol, and/or geraniol.

In some embodiments, the ORF encoding the polypeptide is codon optimized for the host cell. In a particular embodiment, the ORF encoding the polypeptide is codon optimized for E. coli. In a particular embodiment, the ORF encoding the polypeptide is codon optimized for S. cerevisiae.

The present invention provides for a method for reducing one or more isoprenoid, or precursor thereof, comprising: (a) providing a genetically modified host cell of the present invention, or a culture comprising the genetically modified host cell, (b) culturing the genetically modified host cell to produce one or more isoprenoid, or precursor thereof, and expressing the geranylgeranyl reductase (GGR), or polypeptide, and (c) reducing the one or more isoprenoid, or precursor thereof, by the geranylgeranyl reductase (GGR), or polypeptide.

Terpene-based products are of ubiquitous importance to industries specializing in industrial bioscience, pharmaceutical, and food manufacturing. Biological synthesis of terpenes involves fusion of isopentenyl pyrophosphate (IPP) and dimethylallyl pyrophosphate (DMAPP) molecules, resulting in geranyl pyrophosphate (C10), farnesyl pyrophosphate (C15), and geranylgeranyl pyrophosphate (C20) intermediates that are ultimately converted to high-value products of interest.

Partially saturated or fully saturated isoprenoids and intermediates could serve as useful feedstocks for biosynthesis of novel rubbers, biofuels, biochemicals, pharmaceutical and cosmetic compounds. Such partially or fully reduced isoprenoid-based products could be achieved either chemical hydrogenation or via enzymatic reduction using a geranylgeranyl reductase (GGR).

Very few GGRs have been demonstrated so far to reduce intermediates within the terpene biosynthesis pathway. Herein, results are presented that claim many GGRs from various organisms that can reduce multiple products resulting from the terpene biosynthesis pathway including various prenyl pyrophosphate and prenyl alcohols. In addition, some atypical activities of GGR enzymes include their capability of producing the acetate ester of isoprenoid alcohols.

BRIEF DESCRIPTION OF THE DRAWINGS

The foregoing aspects and others will be readily appreciated by the skilled artisan from the following description of illustrative embodiments when read in conjunction with the accompanying drawings.

Scheme 1. Products formed from prenyl alcohols (top) or pyrophosphates (bottom) when incubated with GGR.

Figure 7:
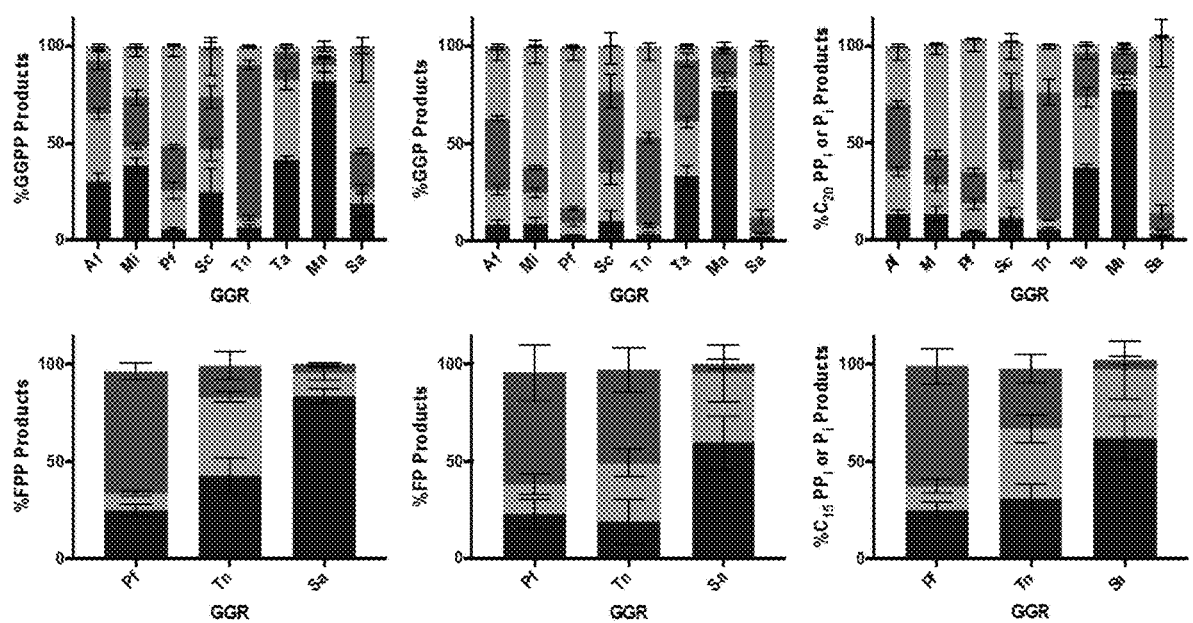

FIG. 7. Endpoint activity profiles for GGR reduction of either GGPP (top) or FPP (bottom) incubated under standard assay conditions for 1 hr. Product distributions are represented as relative percentages of unreduced substrate (blue), $H_2$-products (green), $H_4$-products (red), $H_6$-products (orange), and $H_8$-products (gray) for intact isoprenoid pyrophosphates (left column), hydrolyzed monophosphates (middle column), and the total intensity (right column).

Figure 8:
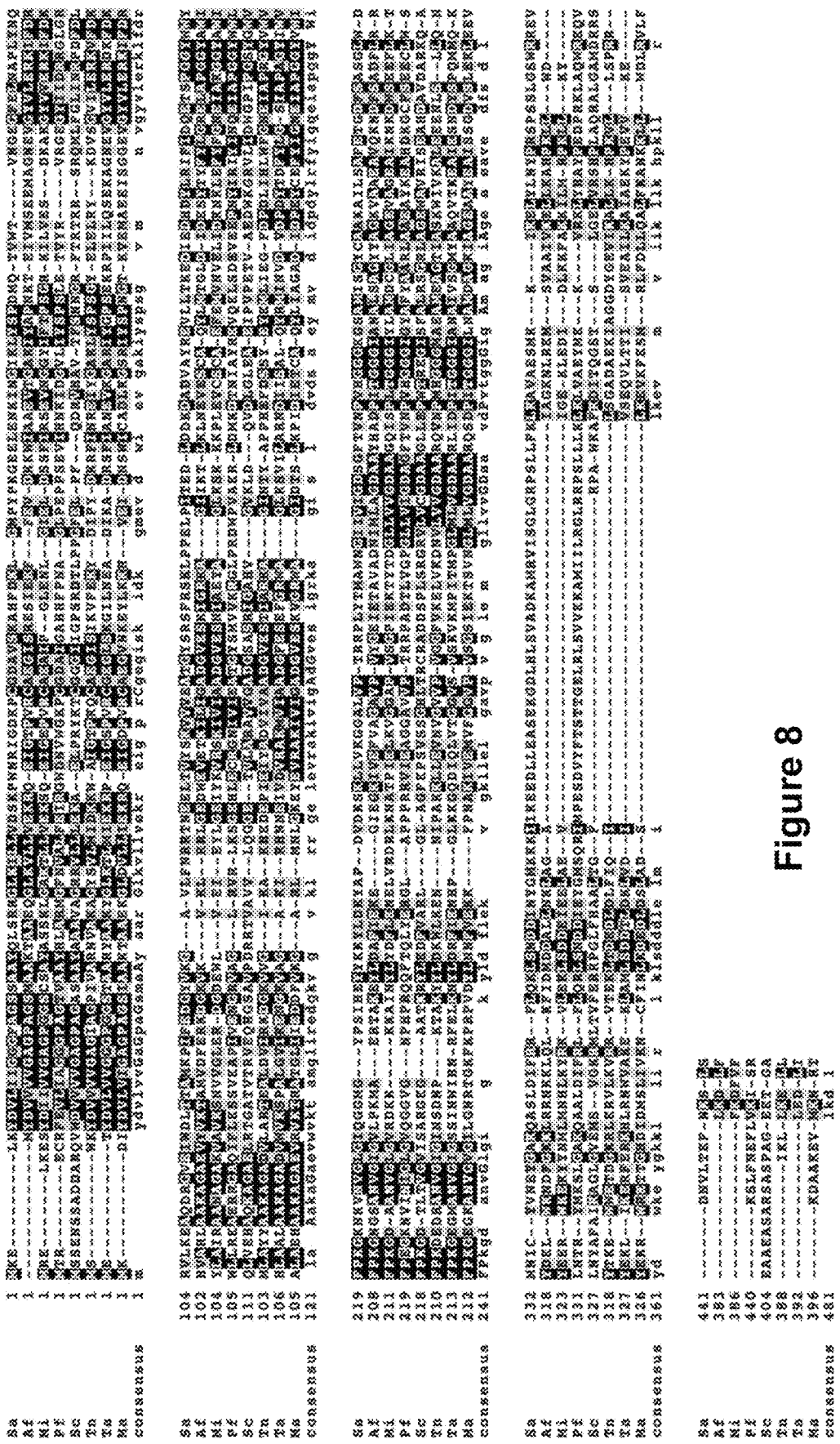

FIG. 8. Multiple sequence alignment of proteins shown to enzymatically reduce either $C_{15}$ or $C_{20}$ prenyl alcohols or prenyl pyrophosphates. Identical residues are highlighted in black, similar residues are highlighted in grey, and gaps are represented by dashes. The amino acid sequences of GGRs of *Sulfolobus acidocaldarius*, *Archaeoglobus fulgidus*, *Methanocaldococcus infernus*, *Pyrolobus fumarii*, *Streptomyces coelicolor*, *Thermococcus nautili*, *Thermoplasma acidophilum*, and *Methanosarcina acetivorans* are depicted (SEQ ID NOs:1-8, respectively).

Figure 9:
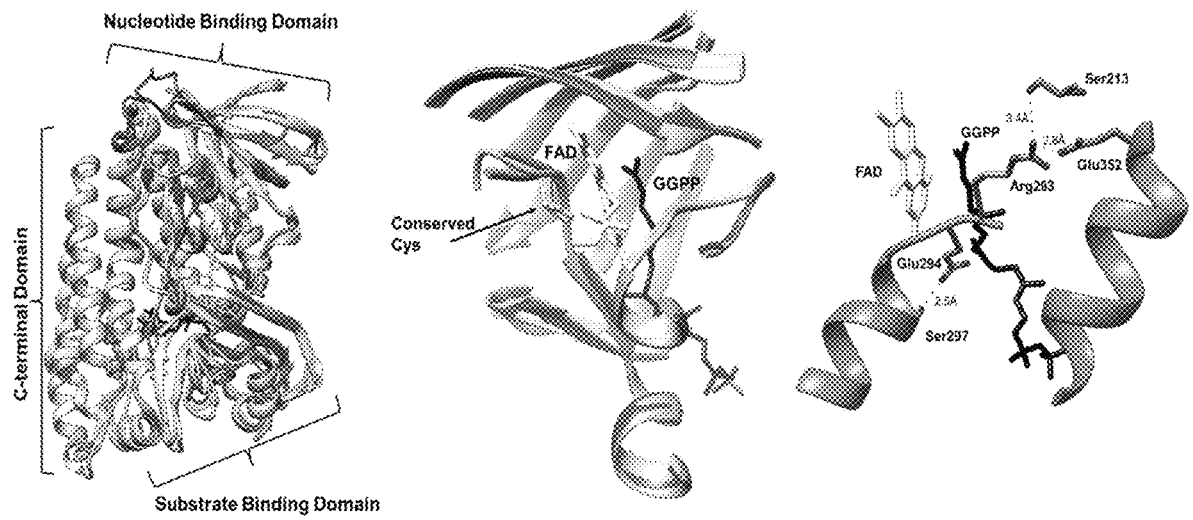

FIG. 9. (Left) Overlaid prediction of modeled protein structures of proteins (Sa, cyan; Pf, tan; Af, fuschia; Mi, green; Tn, red; Ta, gray; Sc, Magenta; Ma, orange) with demonstrated GGR activity using SaGGR (PDB: 4opd) as a template. (Middle) Overlaid alignment of protein active sites of residues within 10 Å of either the FAD isoalloxazine ring or GGPP substrate. The conservation of the active site cysteine found in all GGRs (cf. FIG. 8) are found in proper position to modulate the redox properties of the cofactor. (Right) Examination of the ScGGR active site containing the divergent REG catalytic motif relative to the GGG motif found in archaeal GGRs. Arg293 and Glu294 of ScGGR make critical intradomain hydrogen bonding interactions to accommodate the GGPP binding site.

Figure 10:
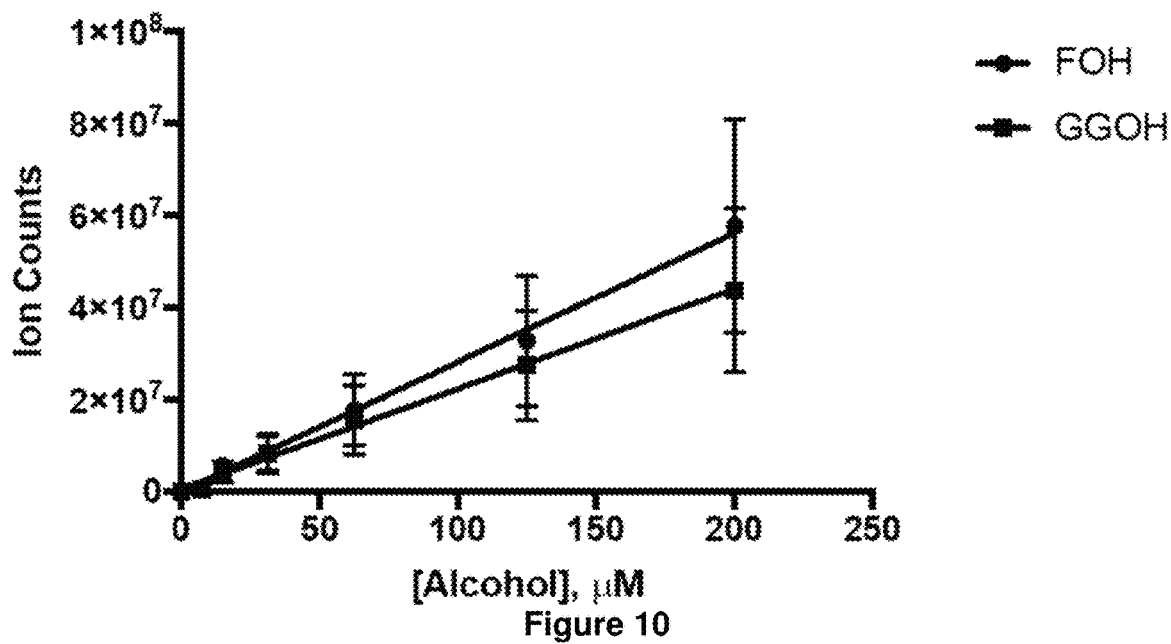

FIG. 10. TIC for neat GGOH (RT=8.4 minutes, top) and FOH (RT=8.0 minutes, middle) substrates. The standard curve for quantifying farnesol (circles) and geranylgeraniol (squares) by GC-MS (bottom) exhibited a linear response for both substrates between 0-200 µM.

Figure 11:
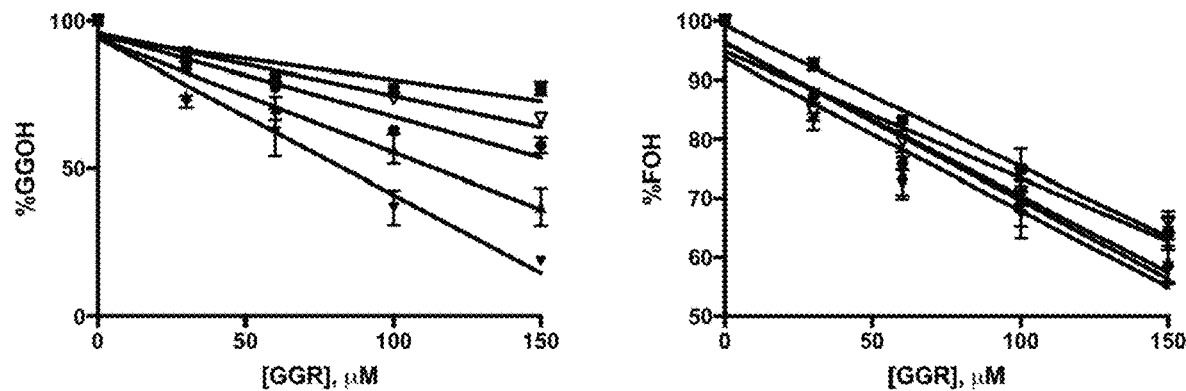

FIG. 11. Verification of accelerated substrate reduction as a function of enzyme concentration for GGOH (left) and FOH (right) for the Af (circles), Mi (squares), Tn (filled triangles), Sa (filled upside down triangles), and Pf (unfilled triangles) GGR enzymes. Specific activities are quoted in Table 2.

Figure 12:
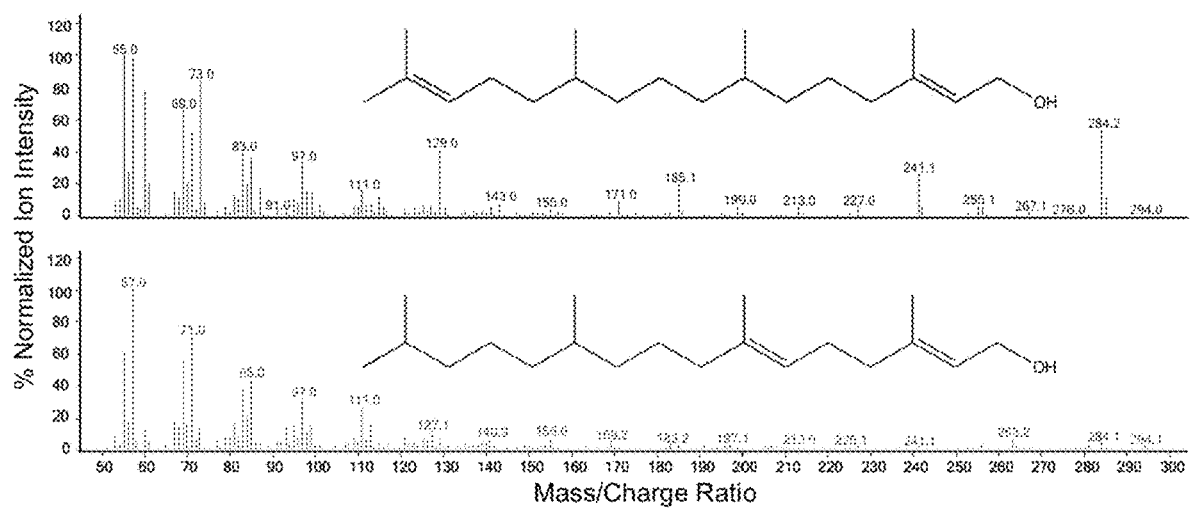

FIG. 12. Comparison of mass spectra between a side product containing one internal prenyl group reduced within $H_4$-GGOH with an 8.0 minutes retention time (Top, black) and the assigned product with the terminal prenyl group reduced in $H_4$-GGOH eluting at 7.7 minutes (Bottom, green). The structures are suggested from NIST database.

Figure 13:
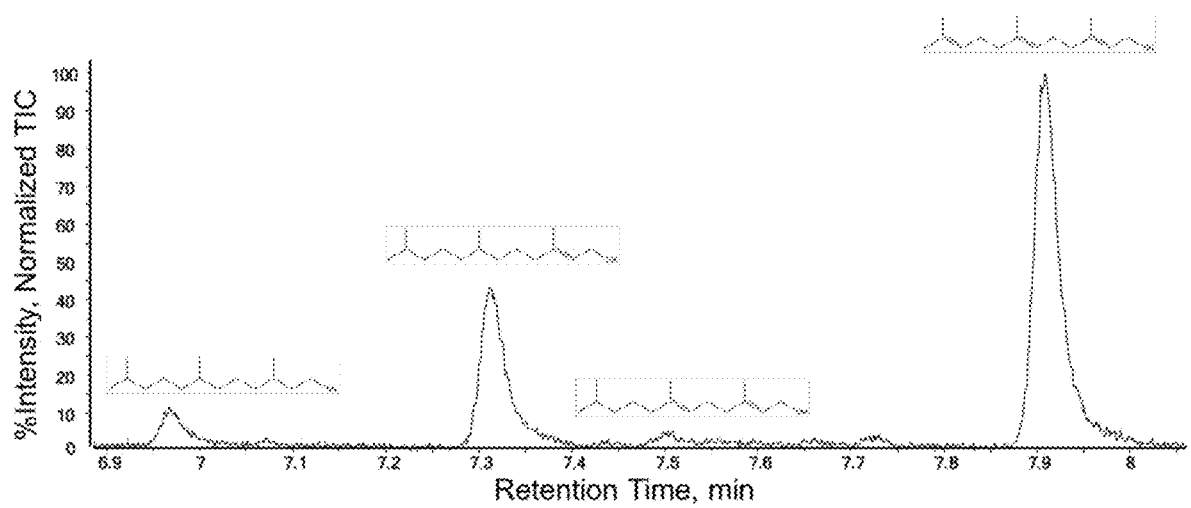

FIG. 13. (Top) Normalized TIC of farnesol activity assay incubated for 2 hr with SaGGR at 50° C., pH 5.5 showing a modest abundance of fully reduced farnesol (RT=7.0±0.1 minutes). For reference, FOH and $H_4$-FOH elute at retention times of 7.9 and 7.3 minutes, respectively. $H_2$-FOH (RT=7.5 minutes) was not observed in any quantifiable abundance. All substrate and cofactor concentrations were held constant.

Figure 14:
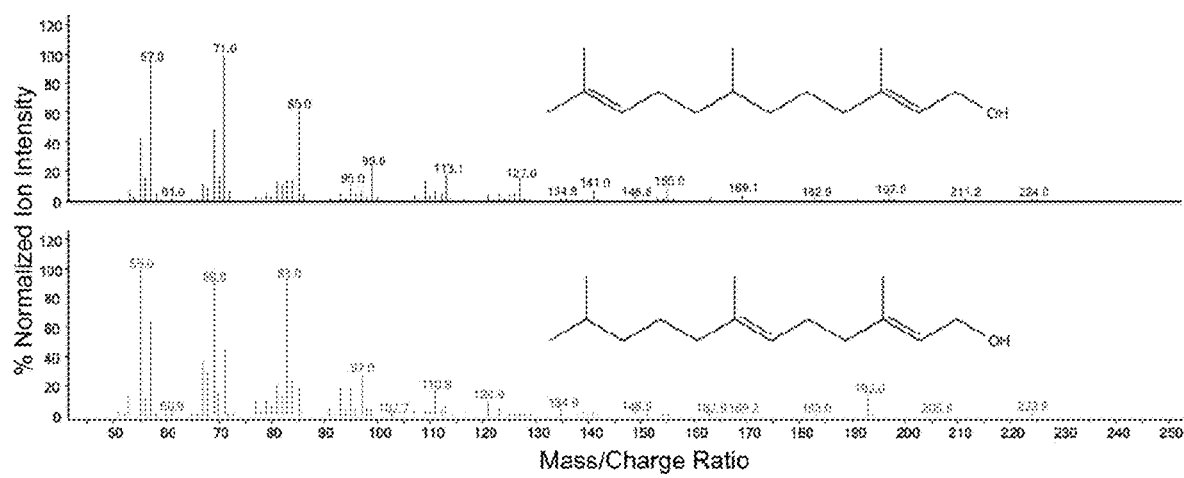

FIG. 14. Comparison of mass spectra between the middle prenyl group reduced within the putative $H_2$-FOH side product eluting at 7.8 minutes retention time (Top, black) and the assigned product with the terminal prenyl group reduced in $H_2$-FOH eluting at 7.6 minutes (Bottom, green).

Figure 15:
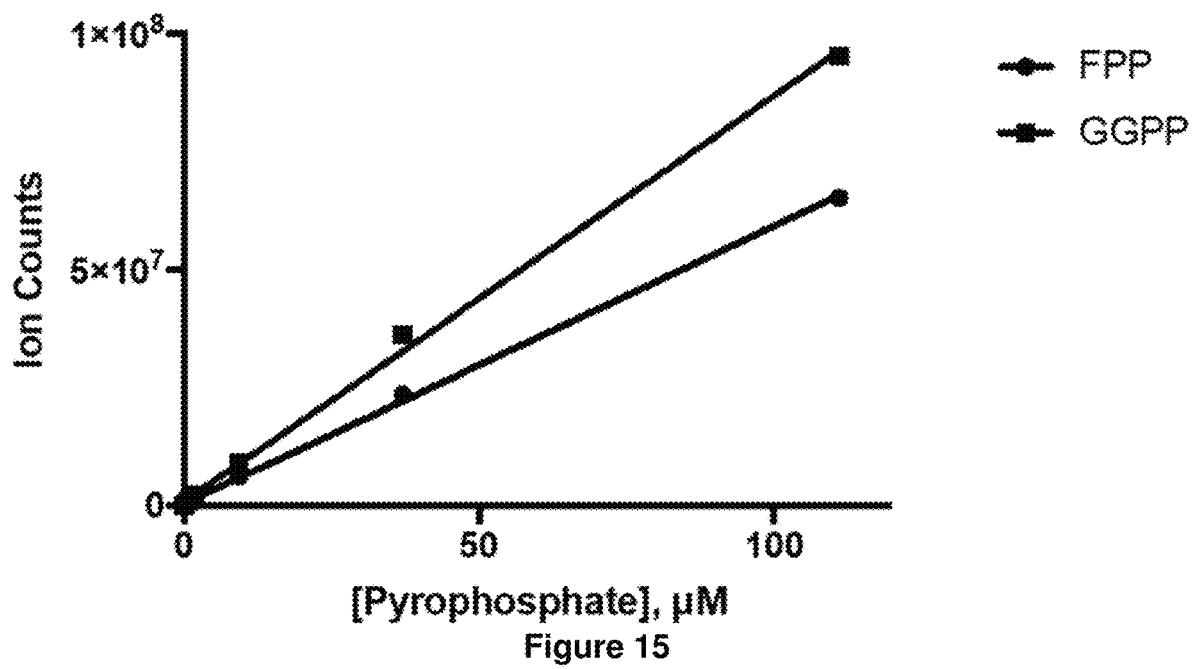

FIG. 15. Standard curve for quantifying FPP (circles) and GGPP (squares) by LC-MS-TOF.

Figure 16:
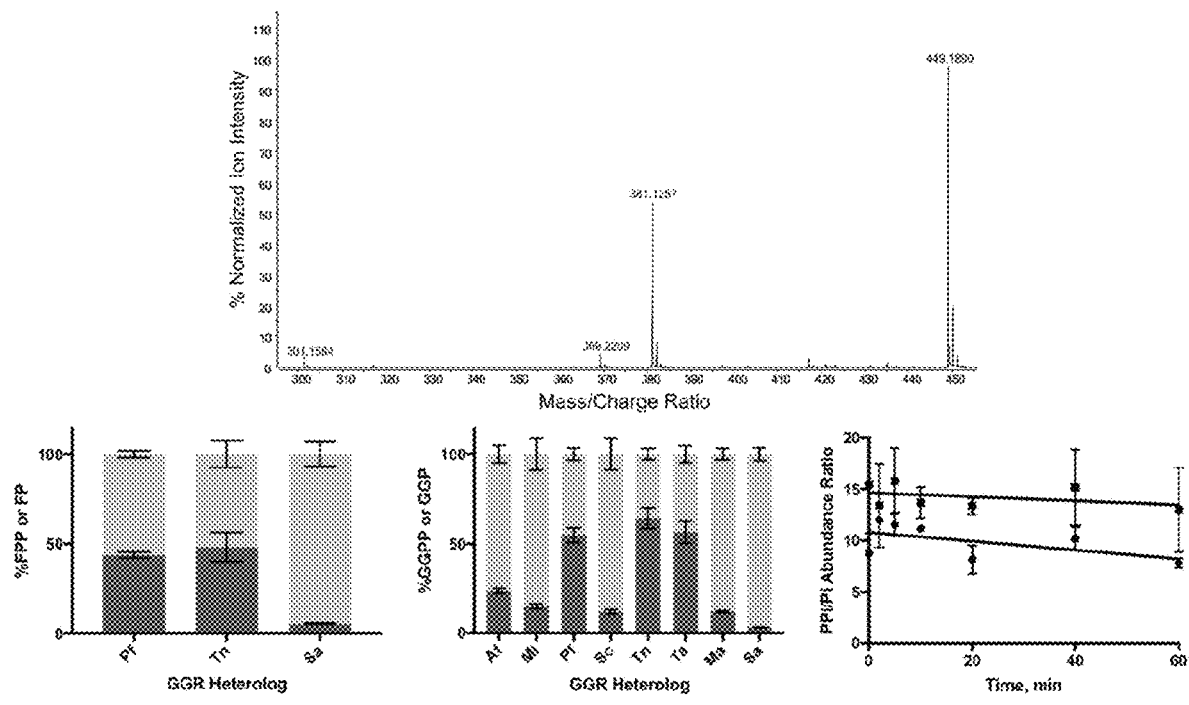

FIG. 16. MS-TOF Spectrum of 100 µM FPP and GGPP standards (Top). (Bottom) Relative abundances of GGPP and GGP (left) or FPP and FP (middle) after incubation under standard assay conditions; negative controls containing all assay components without enzyme (right) rule out the possibility of spontaneous hydrolysis of substrate, as the ratio of pyrophosphate (dark gray) to monophosphate (light gray) products remain constant as a function of time. Reduced products within each mass grouping are included in the total abundance.

Figure 17:
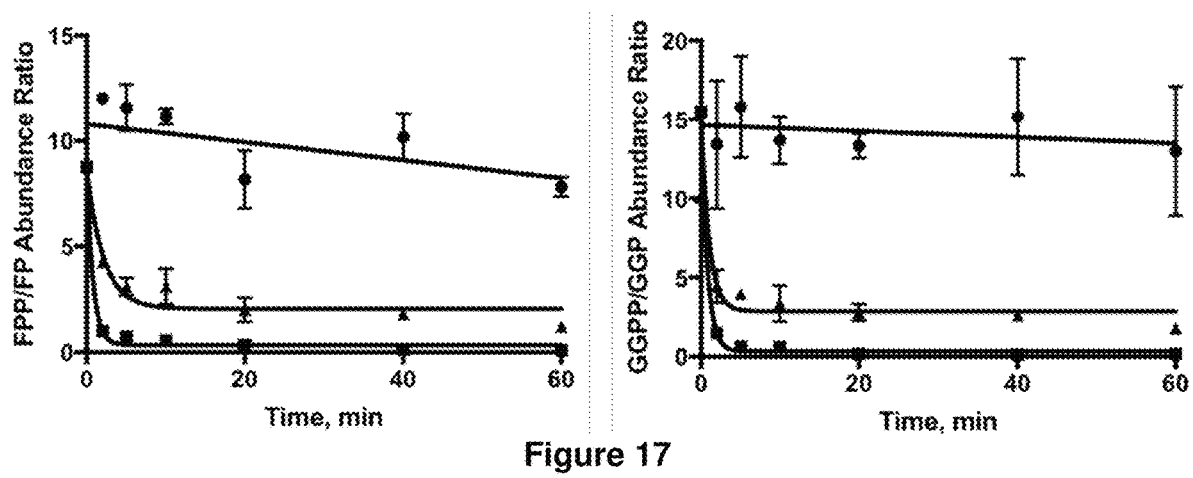

FIG. 17. Demonstration that first-order substrate hydrolysis catalyzed by either SaGGR (squares) or PfGGR(triangles) in either FPP (left) or GGPP (right). The no enzyme control (circles) contained all assay components except enzyme.

Figure 18:
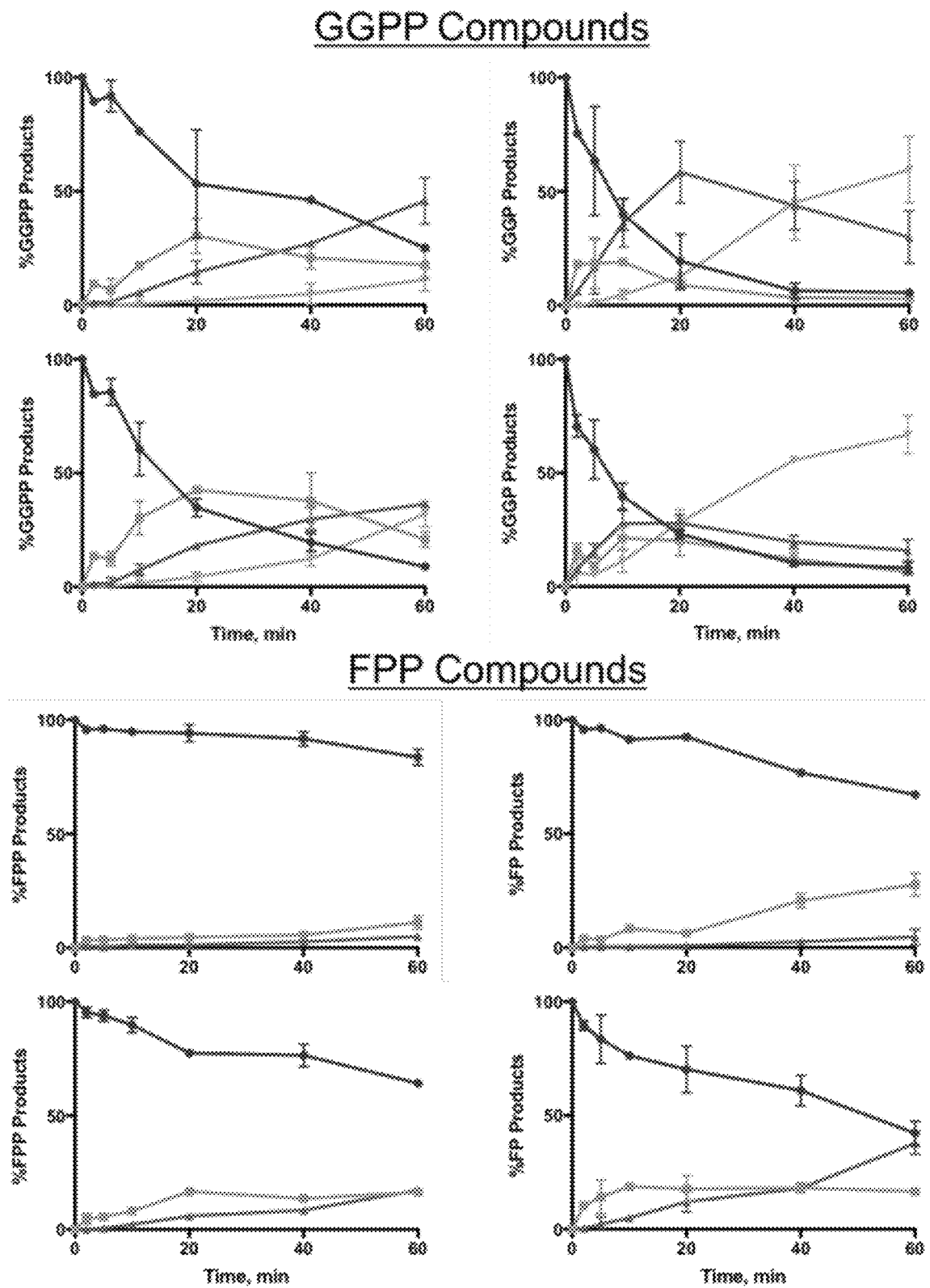

FIG. 18. Timecourse comparison of the standard assay for SaGGR (top row) and PfGGR (bottom row) on either GGPP or FPP substrates. Pyrophosphate abundances are shown in the left column and monophosphate abundances are shown in the right column under each substrate. Products are expressed as having zero reductions (blue), one reduction (green), two reductions (red), or three reductions (orange).

Figure 19A:
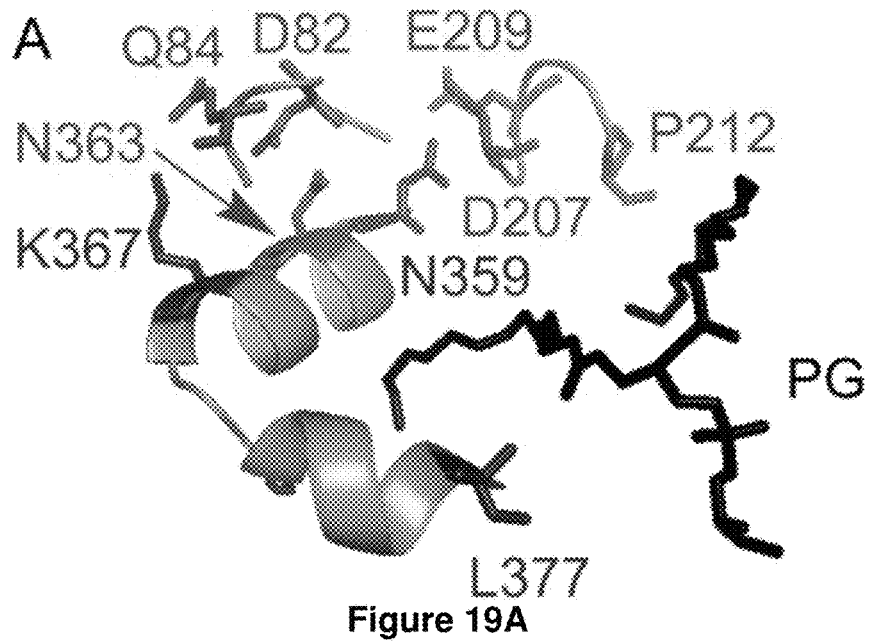

FIG. 19A. Protein crystal structure showing residues involved in salt bridges between the α-helix and β6-β7 loop in SaGGR that encapsulates the end of the substrate (PG) binding pocket.

Figure 19B:
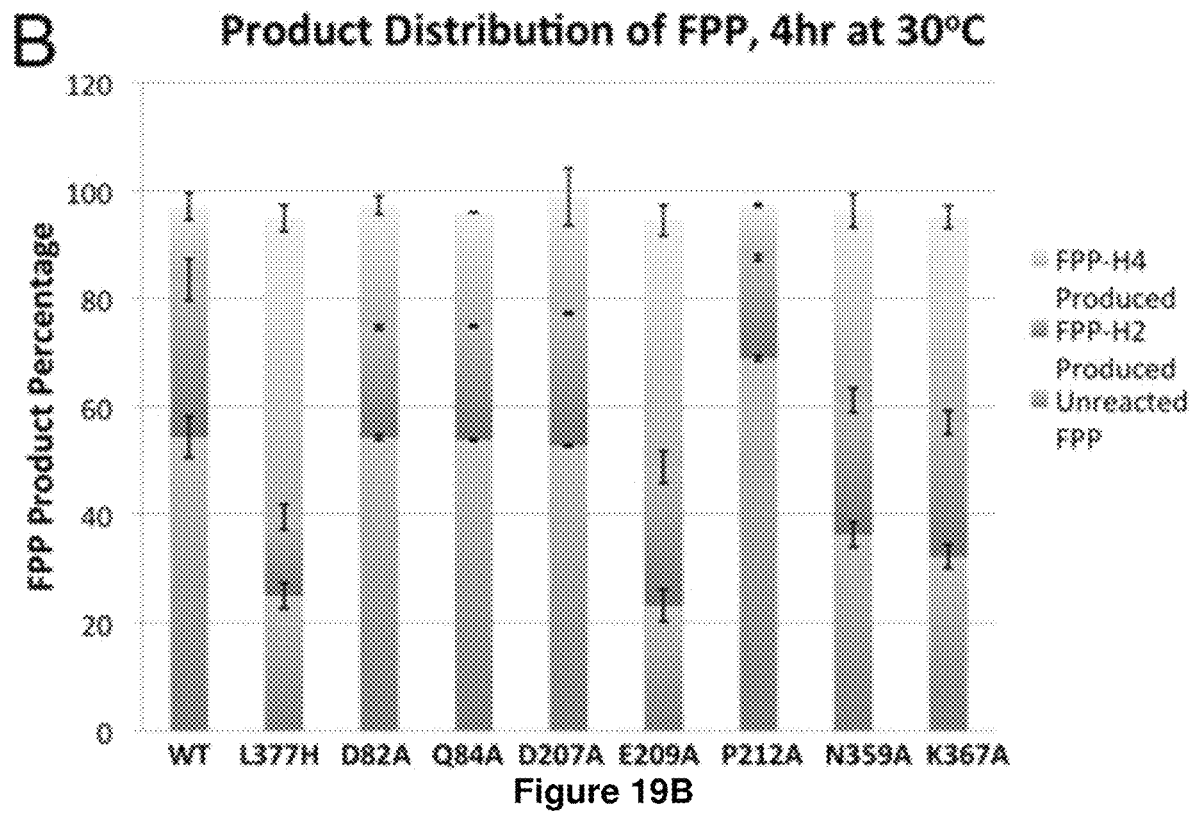

FIG. 19B. Alanine scans have shown that removing these residues shown in FIG. 19A can lead to increased conversion of FPP into its reduced isoprenoid counterparts after four hours.

Figure 20A:
Figure 20A:
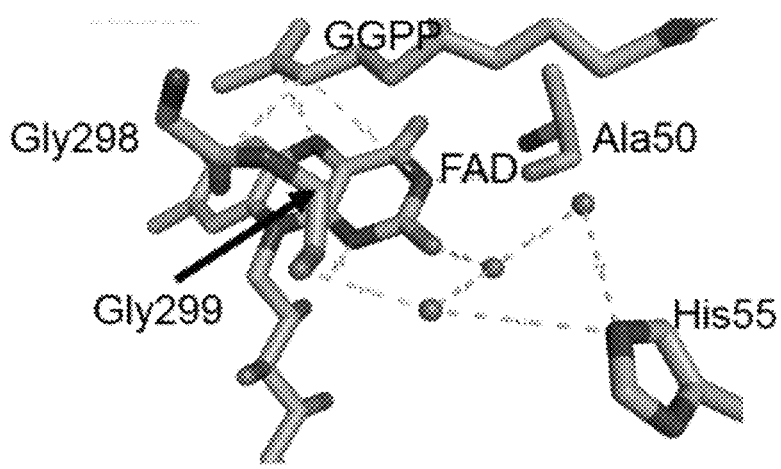

FIG. 20A. Mutation resulting in H2-producs formation. Protein crystal structure showing residues involved in the active site. The amino acid sequences of GGRs of *Sulfolobus acidocaldarius* ("Sa-GGR") and Thermoplasma *acidophilum* "Ta-GGR") are depicted in SEQ ID NO:1 and SEQ ID NO:7.

Figure 20B:
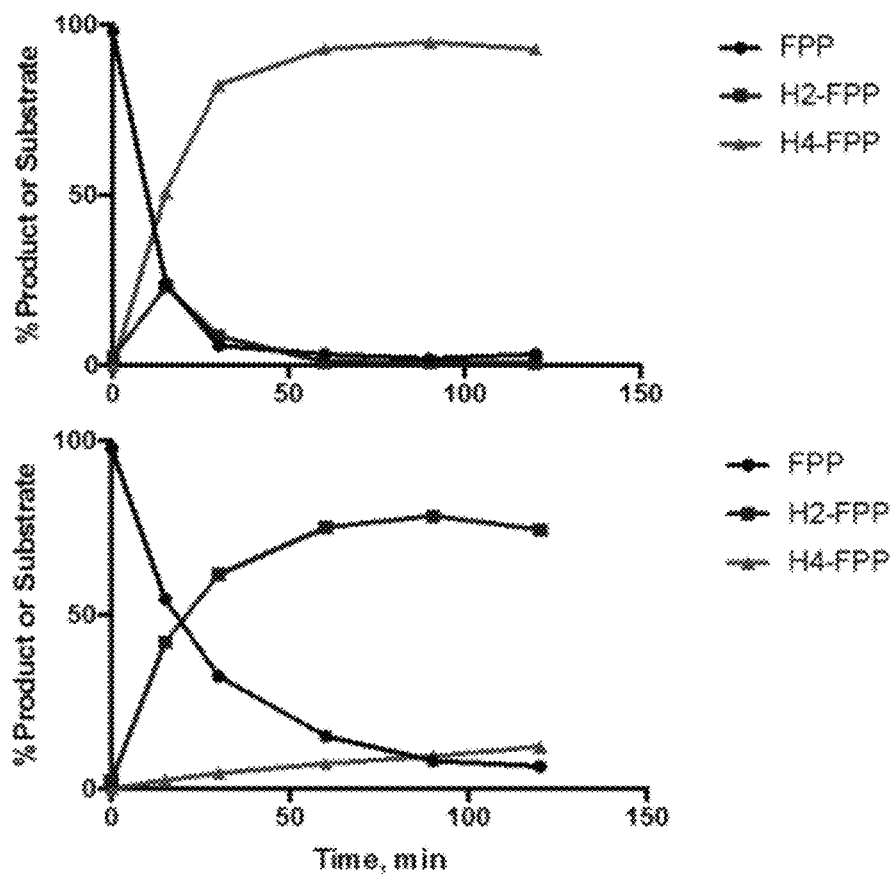

FIG. 20B. Mutation resulting in H2-producs formation. Kinetic time courses of the WT (top) and G298A (bottom) SaGGR variants. While both variants fully consume FPP (black) after two hours of incubation at pH 5.5, 50° C., the wild type preferentially produces $H_4$-FPP (red) while the variants G298A preferentially produces $H_2$-FPP (blue). In G298A, the second reduction is impaired, yielding $H_2$-FPP as main final product.

DETAILED DESCRIPTION OF THE INVENTION

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" as used herein means a value that includes 10% less and 10% more than the value referred to.

The terms "host cell" and "host microorganism" are used interchangeably herein to refer to a living biological cell, such as a microbe, that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

One GGR isolated from Sulfolobus acidocaldarius (SaGGR) has been demonstrated to reduce geranylgeranyl pyrophosphate (GGPP). We have shown for the first time that SaGGR can react promiscuously with a variety of isoprenoid substrates, including geranyl pyrophosphate, farnesyl pyrophosphate, geranylgeraniol, farnesol, and geraniol albeit at slower rates than for GGPP. To this end, a series of terpene synthases or phosphatase (i.e., α- or β-farnesene synthase, or a generic sesqui- or other terpene synthase) could be used on some higher-order isoprenoid pyrophosphate intermediates (i.e., C10-C20) to engineer new pathways for producing partially or fully saturated isoprenoids.

Having demonstrated enzymatic reduction capabilities, we also aim to engineer SaGGR for a variety of alternative applications. The native SaGGR enzyme has been demonstrated to have an activity optimum at ca. 50oC and pH 5.5 in vitro. However, utilizing SaGGR in industrial processes requires its activity optimized at neutral pH and at lower temperatures (i.e., pH 7.4 and 30-37° C.). To this end, alanine scans have shown that altered salt bridges between the α-helix and β6/β7 loop of this enzyme increases enzymatic reductase activity at 30° C. relative to its wild type counterpart. In addition, we showed that GGR engineering can tailor products reducing only 1 instead of 2 double bonds in FPP.

In vitro studies revealed that SaGGR enzymatically reduced not only prenyl pyrophosphates but also isoprenoid alcohols using dithionite as an electron donor. SaGGR can generate fully reduced geranylgeraniol (C20) after one hour at 37oC. Additionally, SaGGR can reduce 2 double bonds in farnesol (C15) under the same conditions. The capability of the enzyme to act on isoprenoid alcohol introduces new pathways to produce reduced isoprenoids by acting not only on the pyrophosphate intermediates of the isoprenoid pathway but also on the final alcohol products (FIG. 1).

reduced isoprenoids, and such action could be facilitated by overexpression of endogenous NADPH-dependent flavodoxin reductases.

The family of GGR enzymes showed a large diversity. Previous reports and articles reported GGR enzymes specialized in reduction of GGPP or DGGPP, dolichol or menaquinone. However, no report has focused on the study of GGR on short chain isoprenoids (pyrophosphate and more surprisingly alcohol). We also showed that some enzymes could perform full reduction on some single chain substrates while this phenomenon has only been observed on DGGPP archaeal membrane component. In addition to reduction activity, we showed that GGR can perform

TABLE 3

Masses used to analyze various products formed from GGR standard assays incubated with prenyl pyrophosphates.

| Compound | Formula | Molecular Mass, Da[a] | Compound | Formula | Molecular Mass, Da[a] |
|---|---|---|---|---|---|
| $C_{20}$ Pyrophosphates | | | $C_{20}$ Monophosphates | | |
| GGPP | $C_{20}H_{30}O_7P_2$ | 449.18635 | GGP | $C_{20}H_{35}O_4P$ | 369.22002 |
| $H_2$-GGPP | $C_{20}H_{38}O_7P_2$ | 451.202 | $H_2$-GGP | $C_{20}H_{37}O_4P$ | 371.23567 |
| $H_4$-GGPP | $C_{20}H_{40}O_7P_2$ | 453.21765 | $H_4$-GGP | $C_{20}H_{39}O_4P$ | 373.25132 |
| $H_6$-GGPP | $C_{20}H_{42}O_7P_2$ | 455.2333 | $H_6$-GGP | $C_{20}H_{41}O_4P$ | 375.26697 |
| $H_8$-GGPP | $C_{20}H_{44}O_7P_2$ | 457.24895 | $H_8$-GGP | $C_{20}H_{43}O_4P$ | 377.28262 |
| $C_{15}$ Pyrophosphates | | | $C_{15}$ Monophosphates | | |
| FPP | $C_{15}H_{28}O_7P_2$ | 381.1237 | FP | $C_{15}H_{27}O_4P$ | 301.1574 |
| $H_2$-FPP | $C_{15}H_{30}O_7P_2$ | 383.1394 | $H_2$-FP | $C_{15}H_{29}O_4P$ | 303.17307 |
| $H_4$-FPP | $C_{15}H_{32}O_7P_2$ | 385.155 | $H_4$-FP | $C_{15}H_{31}O_4P$ | 305.18872 |
| $H_6$-FPP | $C_{15}H_{34}O_7P_2$ | 387.1707 | $H_6$-FP | $C_{15}H_{33}O_4P$ | 307.20437 |

[a]Masses reported are for the deprotonated [M − H]⁻ parent ion in negative mode detection.

While SaGGR serves as a model platform for in vitro studies and metabolic engineering, we have also expanded the number of putative GGRs by exploring activity in a series of selected homologous gene sequences. Many putative GGR protein sequences from plant, bacterial, and archaeal organisms were tested for in vivo expression in E. coli. On the 32 different GGR enzymes over expressed in E. coli, 24 could be produced by E. coli as recombinant protein but only 12 could be purified.

In vitro studies revealed several novel GGRs reducing either isoprenoid pyrophosphates or isoprenoid alcohols. Out of the 12 heterologous genes tested for reductase activity, seven were shown to reduce at least one double bond in the GGPP and FPP.

Some GGR products were observed to undergo phosphoester hydrolysis, yielding the geranylgeranyl phosphate (GGP) product and their respective reduced products containing one or more reduced subunits. While the exact mechanism is unknown, it is believed that phosphoester cleavage conditions are favored under oxidative (i.e., dithionite depleted) conditions, forming reduced GGP byproducts after isoprenoid reduction.

In addition to SaGGR, 4 other GGRs also reduced several isoprenoid alcohols in vitro, notably geranylgeraniol (C20) and farnesol (C15). Two GGRs showed the capability to also reduce geraniol (C10).

Finally, in vivo experiments containing overproducing strains of GGR and FPP revealed that this system was not sufficient for in situ reduction of isoprenoids, even in presence of a ferredoxin partner. However, we observed that GGR had the capability to catalyze the production of farnesyl acetate in vivo as a side reaction. We propose that current in vivo constructs lack the capability necessary to generate dephosphorylation, and I can also generate farnesyl acetate in presence of acetyl-CoA. This category of enzymes remains under exploited and they showed potential beyond their initial main function of reduction. The reason and mechanism of this atypical GGR reaction remain unclear. These enzymes are, in most organisms linked or associated to the membrane, and in this original host condition GGR might mainly act as reductases. Outside of its original host context, this category of enzymes showed lot of other capabilities. However, the fact that these enzymes are mostly membrane might explain why their production, purification and in vitro characterization is challenging. Effectively their stability during purification and exchange buffer often generated precipitations leading to small quantity of enzymes to characterize. To date the activity of these enzymes on non-natural substrates remains low and might explain why we couldn't observe in vivo reduction of FPP or farnesol, but we showed that engineering can be possible to improve their activities.

Partially or fully saturated isoprenoid pyrophosphates or alcohols with various chain length from C10 to C20 could serve very broadly as platform chemicals for companies to more easily create derivatives of antibiotics, vitamins, fragrances, chemicals and fuels. From an industrial biosciences standpoint, energy-dense fuels and novel materials could be synthesized from alternate pathways utilizing fully or partially reduced isoprenoids as a central feedstock. In summary, the potential use of this invention aims to help expand the options available to metabolically engineer terpene-based products of high value and high applicability. This invention can also allow cost reduction for production of reduced isoprenoids.

In addition, these GGR enzymes could also contribute to the production of higher quantity of farnesyl acetate, another compound of industrial interest for fuel and chemical applications within the fragrance and cosmetic industries.

Enzymes, and Nucleic Acids Encoding Thereof

In some embodiments, the polypeptide comprises an amino acid sequence having at least 75%, 80%, 85%, 90%, 95% or 99% identity to an amino acid sequence of a geranylgeranyl reductase (GGR) of Table 1 of Example 1, or Table 1 of Example 2. The polypeptide retains amino acids residues that are recognized as conserved for the enzyme, such as one or more amino acid residues which correspond to L377, D82, Q84, D207, E209, P212, N359, K367, G298, G299, G300, A304, S307, or G308 of *Sulfolobus acidocaldarius* GRR (SaGRR), or one or more conserved or consensus amino acid residues indicated in FIG. 8. The polypeptide may have non-conserved amino acid residues replaced or found to be of a different amino acid, or amino acid(s) inserted or deleted, but which does not affect or has insignificant effect on the enzymatic activity of the polypeptide. The polypeptide has an enzymatic activity that is identical or essentially identical to the enzymatic activity any one of the enzymes described in this specification or in an incorporated reference. The polypeptide may be found in nature or be an engineered mutant thereof.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683, 195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. An example includes lactose promoters (LacI repressor protein changes conformation when contacted with lactose, thereby preventing the LacI repressor protein from binding to the operator). Another example is the tac promoter. (See deBoer et al. (1983) *Proc. Natl. Acad. Sci. USA*, 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming E. coli with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of reduced isoprenoid, or precursor thereof, ensured. When added, the intermediate is present in an excess amount in the culture medium.

Any means for recovering the reduced isoprenoid, or precursor thereof, from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC). Once the reduced isoprenoid, or precursor thereof, is recovered, modification, such as hydrogenation, may be carried out on the reduced isoprenoid, or precursor thereof.

The amino acid sequences of GGRs of *Sulfolobus acidocaldarius, Archaeoglobus fulgidus, Methanocaldococcus infernus, Pyrolobus fumarii, Streptomyces coelicolor, Thermococcus nautili, Thermoplasma acidophilum*, and *Methanosarcina acetivorans* are shown in FIG. 8 (SEQ ID NOS: 1-8, respectively).

Host Cells

The host cells of the present invention are genetically modified in that heterologous nucleic acid have been introduced into the host cells, and as such the genetically modified host cells do not occur in nature. The suitable host cell is one capable of expressing a nucleic acid construct encoding one or more enzymes described herein. The gene(s) encoding the enzyme(s) may be heterologous to the host cell or the gene may be native to the host cell but is operatively linked to a heterologous promoter and one or more control regions which result in a higher expression of the gene in the host cell.

The enzyme can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

Any prokaryotic or eukaryotic host cell may be used in the present method so long as it remains viable after being transformed with a sequence of nucleic acids. Generally, although not necessarily, the host cell is a yeast or a bacterium. In some embodiments, the host cell is a Gram negative bacterium. In some embodiments, the host cell is of the phylum Proteobactera. In some embodiments, the host cell is of the class Gammaproteobacteria. In some embodiments, the host cell is of the order Enterobacteriales. In some embodiments, the host cell is of the family Enterobacteriaceae. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus* taxonomical classes. In some embodiments, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway. Suitable eukaryotic cells include, but are not limited to, fungal, insect or mammalian cells. Suitable fungal cells are yeast cells, such as yeast cells of the *Saccharomyces* genus.

REFERENCES CITED

1. Rohmer M: The discovery of a mevalonate-independent pathway for isoprenoid biosynthesis in bacteria, algae and higher plants. *Nat Prod Rep* 1999, 16(5):565-574.
2. Goldstein J L, Brown M S: Regulation of the mevalonate pathway. *Nature* 1990, 343(6257):425-430.
3. Liang P H, Ko T P, Wang A H J: Structure, mechanism and function of prenyltransferases. *Eur J Biochem* 2002, 269(14):3339-3354.

4. Meadows C W, Kang A, Lee T S: Metabolic Engineering for Advanced Biofuels Production and Recent Advances Toward Commercialization. *Biotechnol J* 2018, 13(1):14.
5. de Carvalho C, da Fonseca MMR: Biotransformation of terpenes. *Biotechnol Adv* 2006, 24(2): 134-142.
6. Guimaraes A G, Serafini M R, Quintans L J: Terpenes and derivatives as a new perspective for pain treatment: a patent review. *Expert Opin Ther Patents* 2014, 24(3): 243-265.
7. Winnacker M, Rieger B: Recent Progress in Sustainable Polymers Obtained from Cyclic Terpenes: Synthesis, Properties, and Application Potential. *ChemSusChem* 2015, 8(15):2455-2471.
8. Ajikumar P K, Tyo K, Carlsen S, Mucha O, Phon T H, Stephanopoulos G: Terpenoids: Opportunities for biosynthesis of natural product drugs using engineered microorganisms. *Mol Pharm* 2008, 5(2):167-190.
9. Dickschat J S: Bacterial terpene cyclases. *Nat Prod Rep* 2016, 33(1):87-110.
10. Pazouki L, Niinemets U: Multi-Substrate Terpene Synthases: Their Occurrence and Physiological Significance. *Front Plant Sci* 2016, 7:16.
11. Bohlmann J, Meyer-Gauen G, Croteau R: Plant terpenoid synthases: Molecular biology and phylogenetic analysis. *Proc Natl Acad Sci U S A* 1998, 95(8):4126-4133.
12. Ajikumar P K, Xiao W H, Tyo K E J, Wang Y, Simeon F, Leonard E, Mucha O, Phon T H, Pfeifer B, Stephanopoulos G: Isoprenoid Pathway Optimization for Taxol Precursor Overproduction in *Escherichia coli*. *Science* 2010, 330(6000):70-74.
13. Lubben M, Morand K: Novel prenylated hemes as cofactors of cytochrome oxidases. Archaea have modified hemes A and O. *J Biol Chem* 1994, 269(34):21473-21479.
14. Martin V J J, Pitera D J, Withers S T, Newman J D, Keasling J D: Engineering a mevalonate pathway in *Escherichia coli* for production of terpenoids. *Nat Biotechnol* 2003, 21(7):796-802.
15. Surmacz L, Swiezewska E: Polyisoprenoids—Secondary metabolites or physiologically important superlipids? *Biochem Biophys Res Commun* 2011, 407(4): 627-632.
16. Zhang F L, Casey P J: Protein prenylation: Molecular mechanisms and functional consequences. *Annu Rev Biochem* 1996, 65:241-269.
17. De Wildeman S M A, Sonke T, Schoemaker H E, May O: Biocatalytic reductions: From lab curiosity to "first choice". *Accounts Chem Res* 2007, 40(12):1260-1266.
18. Smith S, Witkowski A, Joshi A K: Structural and functional organization of the animal fatty acid synthase. *Prog Lipid Res* 2003, 42(4):289-317.
19. Stuermer R, Hauer B, Hall M, Faber K: Asymmetric bioreduction of activated C=C bonds using enoate reductases from the old yellow enzyme family. *Curr Opin Chem Biol* 2007, 11(2):203-213.
20. Toogood H S, Gardiner J M, Scrutton N S: Biocatalytic Reductions and Chemical Versatility of the Old Yellow Enzyme Family of Flavoprotein Oxidoreductases. *ChemCatChem* 2010, 2(8):892-914.
21. Jain S, Caforio A, Driessen A J M: Biosynthesis of archaeal membrane ether lipids. *Front Microbiol* 2014, 5:16.
22. Koga Y, Morii H: Biosynthesis of ether-type polar lipids in archaea and evolutionary considerations. *Microbiol Mol Biol Rev* 2007, 71(1):97-120.
23. Murakami M, Shibuya K, Nakayama T, Nishino T, Yoshimura T, Hemmi H: Geranylgeranyl reductase involved in the biosynthesis of archaeal membrane lipids in the hyperthermophilic archaeon Archaeoglobus fulgidus. *Febs J* 2007, 274(3):805-814.
24. Sato S, Murakami M, Yoshimura T, Hemmi H: Specific partial reduction of geranylgeranyl diphosphate by an enzyme from the thermoacidophilic archaeon Sulfolobus acidocaldarius yields a reactive prenyl donor, not a dead-end product. *J Bacteriol* 2008, 190(11):3923-3929.
25. Mizoguchi T, Isaji M, Yamano N, Harada J, Fujii R, Tamiaki H: Molecular Structures and Functions of Chlorophylls-a Esterified with Geranylgeranyl, Dihydrogeranylgeranyl, and Tetrahydrogeranylgeranyl Groups at the 17-Propionate Residue in a Diatom, Chaetoceros calcitrans. *Biochemistry* 2017, 56(28): 3682-3688.
26. Addlesee H A, Hunter C N: Physical mapping and functional assignment of the geranylgeranyl-bacteriochlorophyll reductase gene, bchP, of Rhodobacter sphaeroides. *J Bacteriol* 1999, 181(23):7248-7255.
27. Hemmi H, Takahashi Y, Shibuya K, Nakayama T, Nishino T: Menaquinone-specific prenyl reductase from the hyperthermophilic archaeon Archaeoglobus fulgidus. *J Bacteriol* 2005, 187(6): 1937-1944.
28. Naparstek S, Guan ZQ, Eichler J: A predicted geranylgeranyl reductase reduces the omega-position isoprene of dolichol phosphate in the halophilic archaeon, Haloferax volcanii. *Biochim Biophys Acta Mol Cell Biol Lipids* 2012, 1821(6):923-933.
29. Sasaki D, Fujihashi M, Iwata Y, Murakami M, Yoshimura T, Hemmi H, Mild K: Structure and Mutation Analysis of Archaeal Geranylgeranyl Reductase. *J Mol Biol* 2011, 409(4):543-557.
30. Xu Q P, Eguchi T, Mathews, II, Rife C L, Chiu H J, Farr C L, Feuerhelm J, Jaroszewski L, Klock H E, Knuth M W et al: Insights into Substrate Specificity of Geranylgeranyl Reductases Revealed by the Structure of Digeranylgeranylglycerophospholipid Reductase, an Essential Enzyme in the Biosynthesis of Archaeal Membrane Lipids. *J Mol Biol* 2010, 404(3):403-417.
31. Isobe K, Ogawa T, Hirose K, Yokoi T, Yoshimura T, Hemmi H: Geranylgeranyl Reductase and Ferredoxin from Methanosarcina acetivorans Are Required for the Synthesis of Fully Reduced Archaeal Membrane Lipid in *Escherichia coli* Cells. *J Bacteriol* 2014, 196(2):417-423.
32. Ogawa T, Isobe K, Mori T, Asakawa S, Yoshimura T, Hemmi H: A novel geranylgeranyl reductase from the methanogenic archaeon Methanosarcina acetivorans displays unique regiospecificity. *Febs J* 2014, 281(14): 3165-3176.
33. Kung Y, McAndrew R P, Xie X K, Liu C C, Pereira J H, Adams P D, Keasling J D: Constructing Tailored Isoprenoid Products by Structure-Guided Modification of Geranylgeranyl Reductase. *Structure* 2014, 22(7): 1028-1036.
34. Blaser H U, Malan C, Pugin B, Spindler F, Steiner H, Studer M: Selective hydrogenation for fine chemicals: Recent trends and new developments. *Adv Synth Catal* 2003, 345(1-2):103-151.
35. Stephan D W: Frustrated Lewis Pairs: From Concept to Catalysis. *Accounts Chem Res* 2015, 48(2):306-316.
36. Noyori R, Hashiguchi S: Asymmetric transfer hydrogenation catalyzed by chiral ruthenium complexes. *Accounts Chem Res* 1997, 30(2):97-102.

37. Maurer S, Hauer B, Bonnekessel M, Faber K, STÜCKLER C: A process for the enzymatic reduction of enoates. In.: Google Patents; 2011.
38. Shpilyov A V, Zinchenko V V, Shestakov S V, Grimm B, Lokstein H: Inactivation of the geranylgeranyl reductase (ChlP) gene in the cyanobacterium Synechocystis sp PCC 6803. *Biochim Biophys Acta-Bioenerg* 2005, 1706(3):195-203.
39. Keller Y, Bouvier F, D'Harlingue A, Camara B: Metabolic compartmentation of plastid prenyllipid biosynthesis—Evidence for the involvement of a multifunctional geranylgeranyl reductase. *Eur J Biochem* 1998, 251(1-2):413-417.
40. Eichler J, Guan Z Q: Lipid sugar carriers at the extremes: The phosphodolichols Archaea use in N-glycosylation. *Biochim Biophys Acta Mol Cell Biol Lipids* 2017, 1862(6):589-599.
41. Edgar RC: MUSCLE: multiple sequence alignment with high accuracy and high throughput. *Nucleic Acids Res* 2004, 32(5):1792-1797.
42. Kearse M, Moir R, Wilson A, Stones-Havas S, Cheung M, Sturrock S, Buxton S, Cooper A, Markowitz S, Duran C et al: Geneious Basic: An integrated and extendable desktop software platform for the organization and analysis of sequence data. *Bioinformatics* 2012, 28(12):1647-1649.
43. Stamatakis A: RAxML version 8: a tool for phylogenetic analysis and post-analysis of large phylogenies. *Bioinformatics* 2014, 30(9): 1312-1313.
44. Letunic I, Bork P: Interactive tree of life (iTOL) v3: an online tool for the display and annotation of phylogenetic and other trees. *Nucleic Acids Res* 2016, 44(W1):W242-W245.
45. Biasini M, Bienert S, Waterhouse A, Arnold K, Studer G, Schmidt T, Kiefer F, Cassarino T G, Bertoni M, Bordoli L et al: SWISS-MODEL: modelling protein tertiary and quaternary structure using evolutionary information. *Nucleic Acids Res* 2014, 42(W1):W252-W258.
46. Pettersen E F, Goddard T D, Huang C C, Couch G S, Greenblatt D M, Meng E C, Ferrin T E: UCSF chimera—A visualization system for exploratory research and analysis. *J Comput Chem* 2004, 25(13):1605-1612.
47. Rodriguez S, Kirby J, Denby C M, Keasling J D: Production and quantification of sesquiterpenes in *Saccharomyces cerevisiae*, including extraction, detection and quantification of terpene products and key related metabolites. *Nat Protoc* 2014, 9(8):1980-1996.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Discovery of Novel Geranylgeranyl Reductases and Characterization of their Substrate Promiscuity Background: Geranylgeranyl reductase (GGR) is a flavin-containing redox enzyme that hydrogenates a variety of unactivated polyprenyl substrates, which are further processed mostly for lipid biosynthesis in archaea or chlorophyll biosynthesis in plants. To date, only a few GGR genes have been confirmed to reduce polyprenyl substrates in vitro or in vivo.

Results: In this work, we aimed to expand the confirmed GGR activity space by searching for novel genes that function under amenable conditions for microbial mesophilic growth in conventional hosts such as *Escherichia coli* or *Saccharomyces cerevisiae*. 31 putative GGRs were selected to test for potential reductase activity in vitro on farnesyl pyrophosphate (FPP), geranylgeranyl pyrophosphate (GGPP), farnesol (FOH), and geranylgeraniol (GGOH). We report the discovery of several novel GGRs exhibiting significant activity toward various polyprenyl substrates under mild conditions (i.e., pH 7.4, T=37° C.), including the discovery of a novel bacterial GGR isolated from *Streptomyces coelicolor*. In addition, we uncover new mechanistic insights within several GGR variants, including GGR-mediated phosphatase activity toward polyprenyl pyrophosphates and the first demonstration of completely hydrogenated GGOH and FOH substrates.

Conclusion: These collective results enhance the potential for metabolic engineers to manufacture a variety of isoprenoid-based biofuels, polymers, and chemical feedstocks in common microbial hosts such as *E. coli* or *S. cerevisiae*.

Biomanufacturing of reduced isoprenoid compounds requires a reductase activity under biologically relevant conditions required by bacterial and yeast strains (i.e., at 30-37° C., at pH 7). In this study, we sought to increase the diversity space of GGRs by testing several dozen putative GGR sequences across a broad phylogeny, and we proceeded to test their associated substrate promiscuities under conditions ideal for microbial manufacturing (Scheme 1). Herein, we present significant insights on GGR activities that encompass newly confirmed GGR enzymes, novel substrate activities, and promiscuous catalysis.

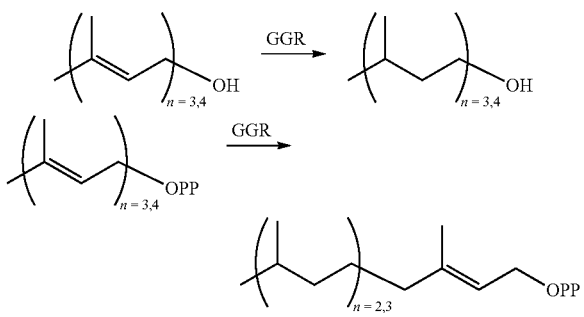

Scheme 1

RESULTS AND DISCUSSION

Selection and Expression of Potential GGR Candidates.

Figure 1A:
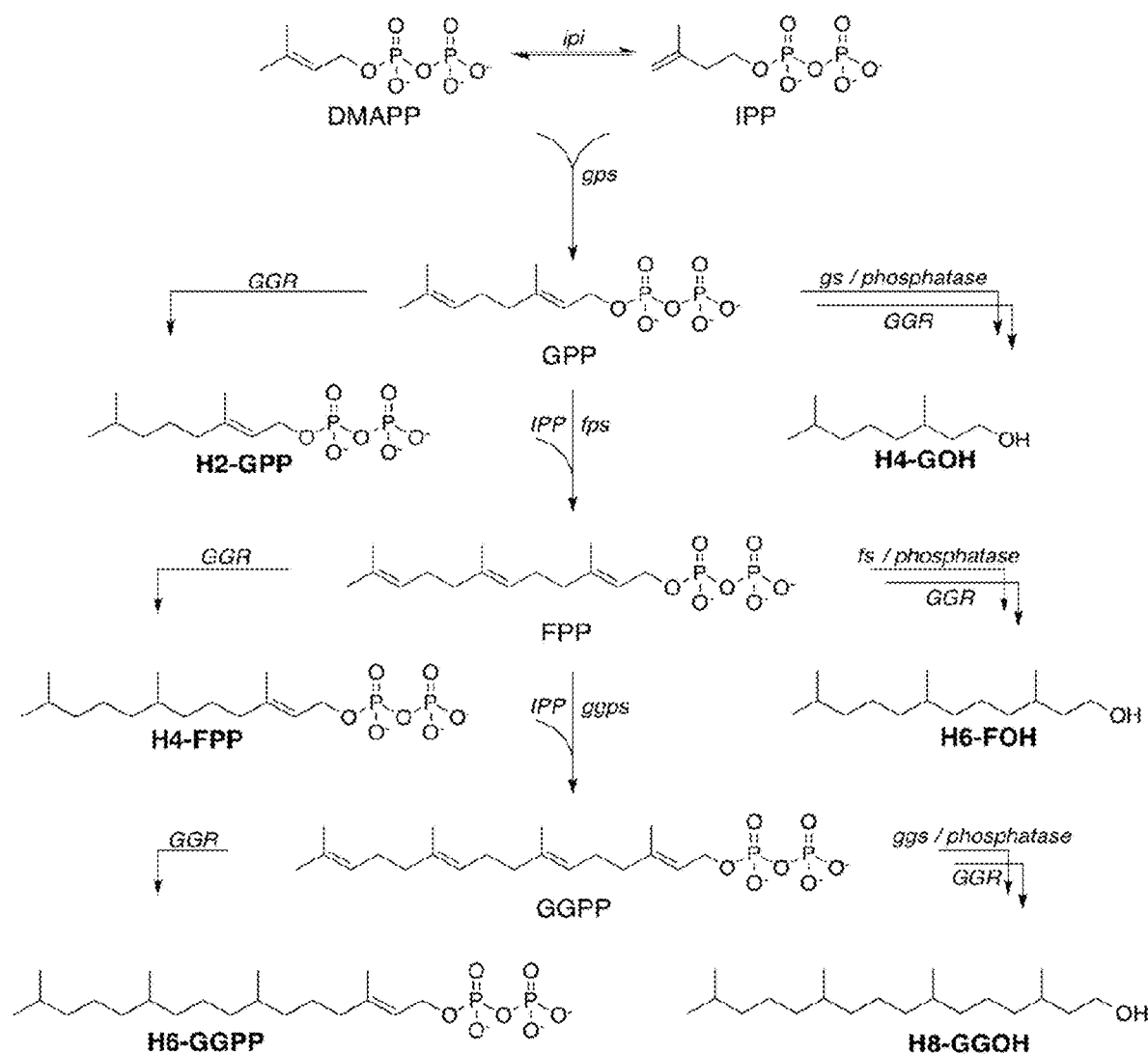
FIG. 1A. Proposed routes for the production of partially or fully reduced terpenes via engineered mevalonate or deoxyxylulose-5-phosphate pathways. The main products of either pathway are isopentenyl pyrophosphate (IPP) or dimethylallyl pyrophosphate (DMAPP). These precursors are fused to make larger terpenes such as geranyl pyrophosphate (GPP-$C_{10}$), farnesyl pyrophosphate (FPP-$C_{15}$), and geranylgeranyl pyrophosphate (GGPP-$C_{20}$). Geranyl pyrophosphate synthase (gps), farnesene pyrophosphate synthase (fps), and geranylgeranyl pyrophosphate synthase (ggps) are enzymes that facilitate production of higher-order terpenes. These terpenes can be converted to their cognate alcohols by phosphatases or alcohol synthases, including geraniol synthase (gs), farnesol synthase (fs) or geranylgeraniol synthase (ggs). The geranylgeranyl reductase from Sulfolobus acidocaldarius (SaGGR) can reduce GPP to dihydrogeranyl pyrophosphate ($H_2$-GPP), FPP to tetrahydrofarnesyl pyrophosphate ($H_4$-FPP) and GGPP to hexahydrogeranylgeranyl pyrophosphate ($H_6$-GGPP). In the case of isoprenoid alcohols, SaGGR is capable of complete reduction, yielding tetrahydrogeraniol ($H_4$-GOH), hexahydrofarnesol ($H_6$-FOH) and octahydrogeranylgeraniol ($H_8$-GGOH).
Figure 1B:
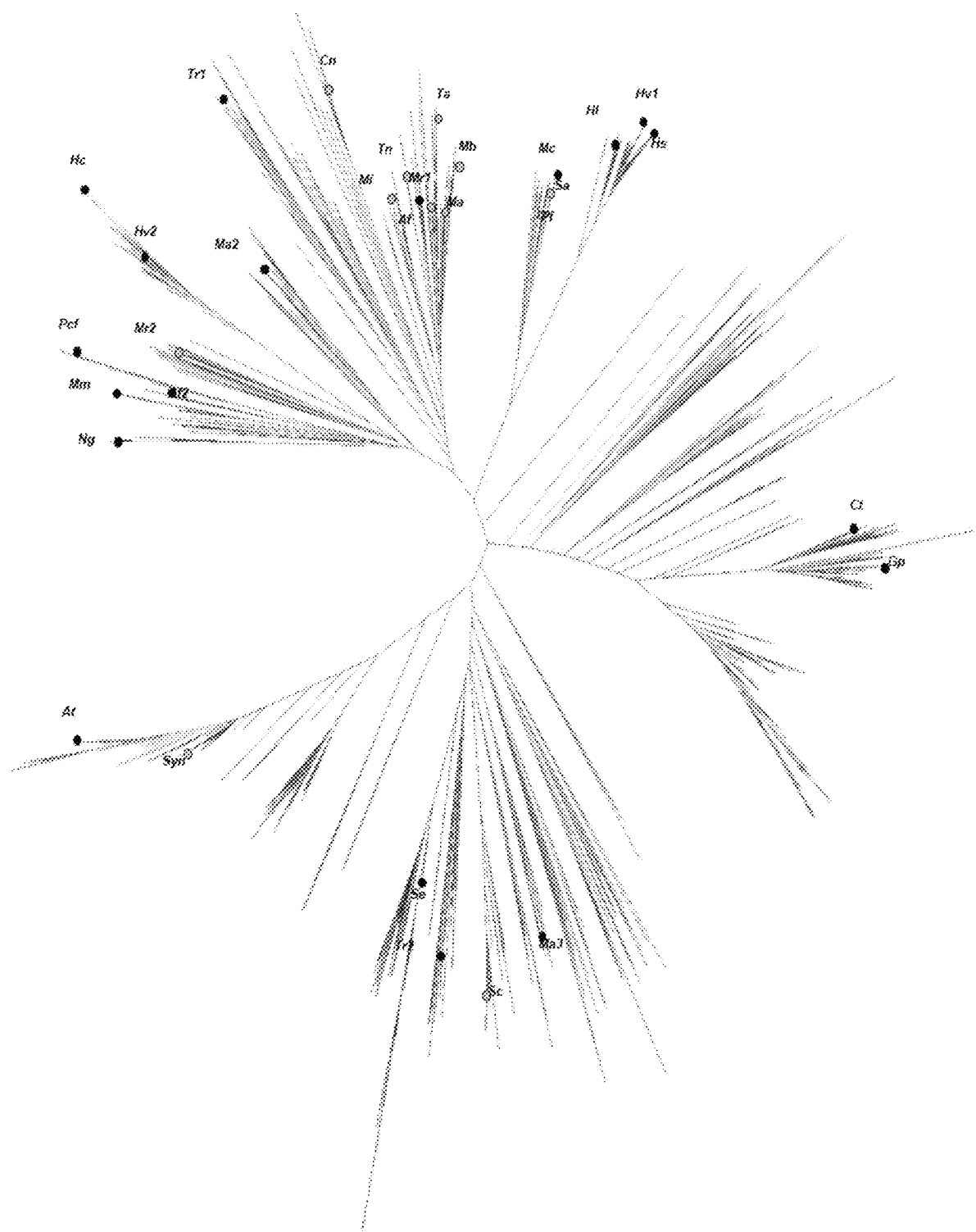
FIG. 1B. Phylogenetic tree representing the diversity of the GGR family of enzymes. The tree includes 1787 sequences of predicted GGR's from the InterPro database. Putative GGRs were selected from various organisms encompassing archaea (red), bacteria (purple), cyanobacteria (blue), alga (cyan), and plants (green). Black circles represent GGRs selected to test for isoprenoid reductase activity within this study; orange circles represent soluble proteins successfully purified and tested for reductase activity. The organismal abbreviations are listed described in Table 3.

FIG. 1A shows proposed routes for the production of partially or fully reduced terpenes via engineered mevalonate or deoxyxylulose-5-phosphate pathways. The Interpro database (EMBL-EBI) predicts over 8,000 proteins present within the GGR family (InterPro code: IPR011777), with many homologous genes containing sequence identities as low as 20-30%. After sequence alignment, a phylogeny tree includes 1,787 sequences of predicted GGR from the InterPro database. A few GGRs within this database have been confirmed by other groups to reduce a wide variety of large prenylated substrates, including GGPP, DGGGP, geranylgeranylchlorophyll, menaquinone, and dolichol [25-32]. To investigate the in vitro prenyl reductase potential of other genes within the GGR family, we selected some with conserved sequence homologies to known GGR's and other more distant sequences. As observed in FIG. 1B, it was possible to observe some subgroups with conserved sequences (e.g. Mc, Sa, Pf or H1, Hv1, Hs). Most of the sequences in the predicted GGR family, however, are very divergent. Our selection was then based on kingdom and diversity of species (e.g. archaea, algae, plant, cyanobacteria, and bacteria), on environmental diversity (e.g. temperatures, pH, aerobic or anaerobic), as well as particular characteristics of some strains (e.g. *Corynebacterium terpenotabidum* or *Gordonia polyisoprenivorans* are actinomycetes capable of degrading squalene and rubber reciprocally). A few GGRs were also selected more randomly for their atypical sequences (FIG. 1B).

Figure 2:
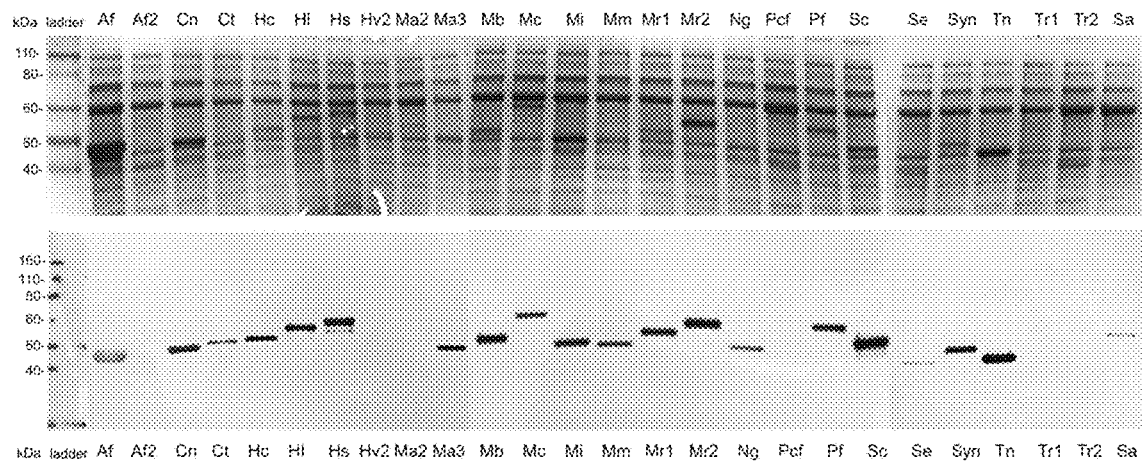
FIG. 2. Various putative GGR's expression in E. coli BL21 (DE3) harboring the pG-KJE8 plasmid. SDS-PAGE (top) and Western blot using anti-His antibody (bottom) verify protein overexpression in crude lysates at the expected masses. Only 26 out of the 31 selected GGR are shown in this figure.

The 31 selected genes were codon optimized for *E. coli* expression and were all successfully transformed into *E. coli*. Initial expression attempts were not successful for many proteins using *E. coli* BL21 (DE3). However, by using *E. coli* BL21 (DE3) strain harboring the commercially available pG-KJE8 plasmid overexpressing several *E. coli* chaperones, 24 of 31 strains overexpressed soluble proteins at the target masses for each protein, with each protein's presence in cell lysates confirmed by western blot containing the anti-His tag antibody (FIG. 2). Out of them, only 12 proteins (Af, Cn, Ma, Mb, Mi, Mr2, Pf, Sa, Sc, Syn, Ta, and Tn) were obtained in sufficiently large quantities needed for activity assays after a standard purification and concentration process conducted at pH 7.4.

Activity of GGR on isoprenoid alcohol using WT SaGGR as model.

Figure 3A:
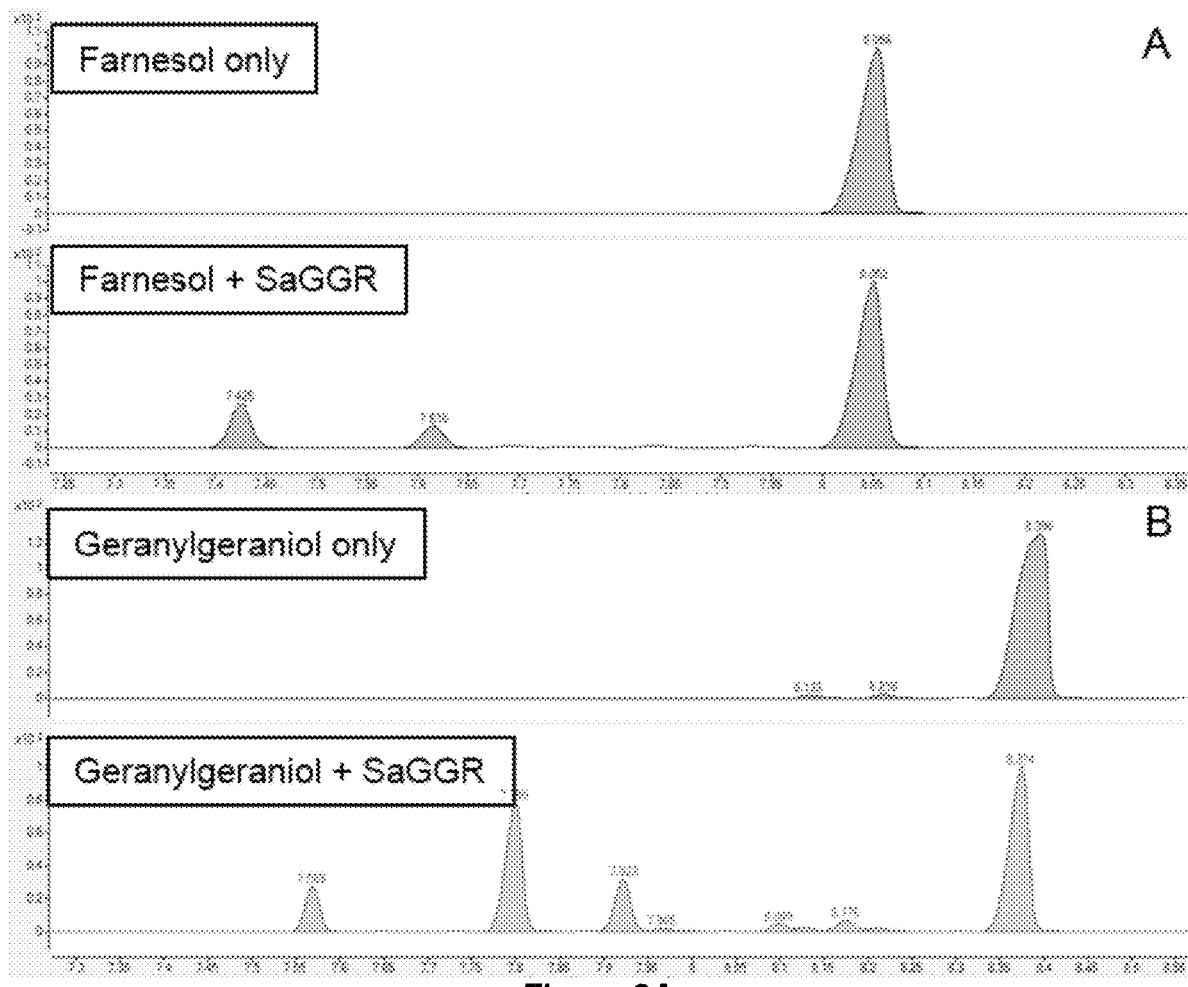
FIG. 3A. Activity of SaGGR on isoprenoid alcohol. Normalized total ion chromatogram traces derived via GC-MS analysis. Both farnesol (top) and gernylgeraniol (bottom) substrates yield reduced product peaks after incubating 500 μM of each respective substrate with 100 μM SaGGR for 1 hr at 37° C. The retention times for farnesol (FOH), $H_2$-FOH, and $H_4$-FOH elute at 8.0, 7.6, and 7.4 minutes, respectively. For geranylgeraniol (GGOH), unreacted substrate elutes at 8.4 minutes. Its associated reduced products elute at 8.1, 7.9, 7.8, and 7.6 minutes for $H_2$-GGOH, $H_4$-GGOH, $H_6$-GGOH, $H_8$-GGOH. Mass spectra of geranylgeraniol and its reduced counterparts after incubation with SaGGR. Each mass spectrum was derived from each peak's maximum ion intensity at the retention times listed previously.

SaGGR activity on isoprenoid alcohol was detested. This enzyme is capable of reducing farnesol and geranylgeraniol. Assay performed for 1 hour 37° C., pH 7.4 (condition aligned with industrial processes), showed that the enzyme is producing H2- and H4-farnesol (FIG. 3A) and H2-, H4-, H6- and H8-geranylgeraniol (FIG. 3A). FIG. 7C confirm that the pic generated by the GGR on geranylgeraniol at 8.1, 7.9, 7.8, and 7.6 minutes are indeed H2-GGOH, H4-GGOH, H6-GGOH, H8-GGOH. The fully saturated isoprenoid product has previously been observed only on naturel substrate of the enzyme the DGGGP. The full reduction was observed on the non-natural substrate geranylgeraniol for the first time In vitro activity with isoprenoid alcohols.

The 12 soluble proteins successfully isolated were tested for reductase activity on GGOH and FOH, and products obtained after enzymatic incubation were analyzed by GC-MS.

Figure 3B:
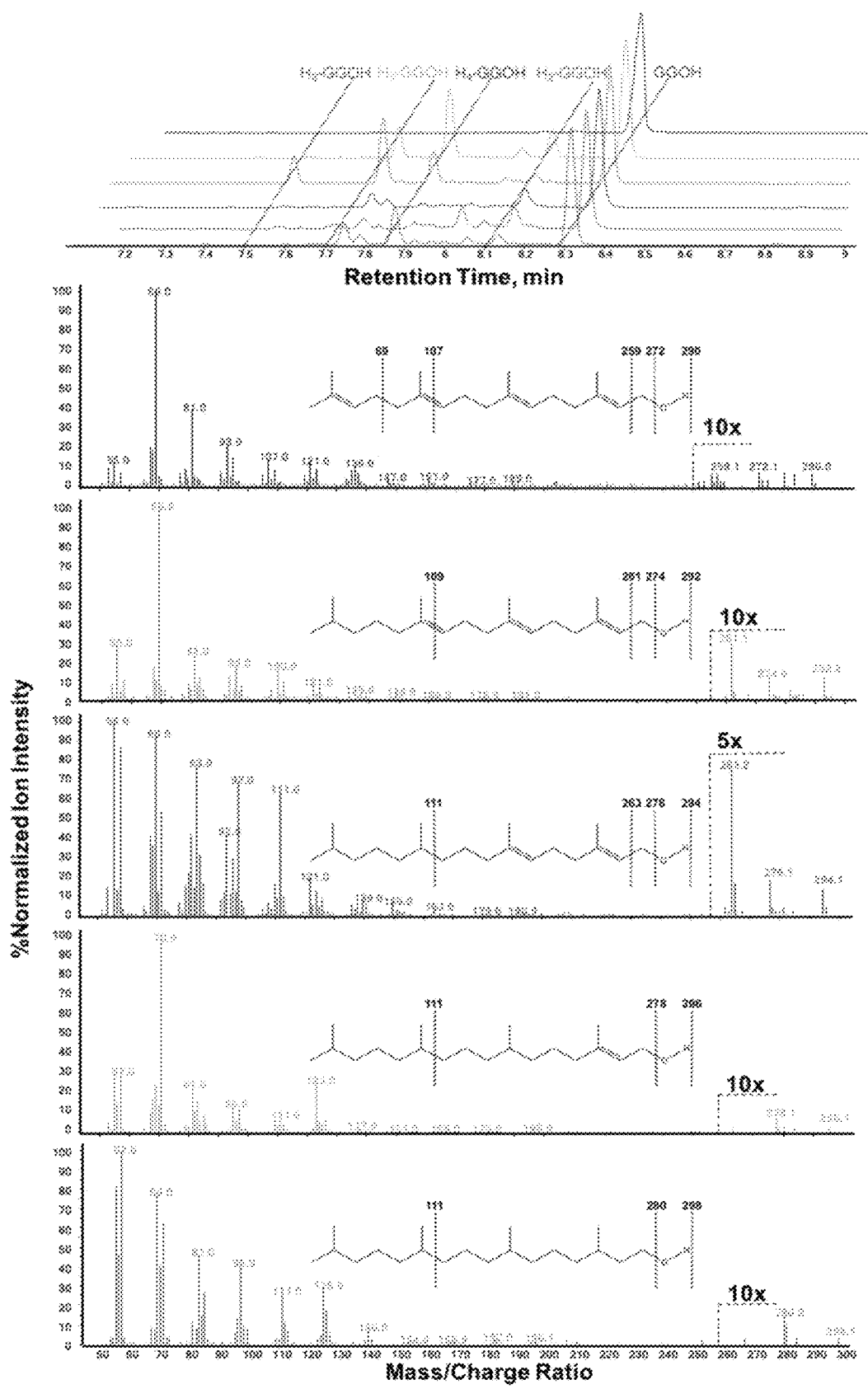
FIG. 3B. (Top) Normalized TIC profiles of five putative GGRs (Af, red; Pf, green; Mi, blue; Sa, magenta; Tn, orange; No Enzyme, black) found to reduce GGOH (RT=8.31 min) to $H_2$-GGOH (RT=8.12 min), $H_4$-GGOH (RT=7.85 min), $H_6$-GGOH (RT=7.72 min), and $H_8$-GGOH (RT=7.52 min) upon 1 hr incubation under standard assay conditions. All peaks elute with a relative error of ±0.05 minutes. (Bottom) The associated mass spectra for GGOH (blue), $H_2$-GGOH (green), $H_4$-GGOH (red), $H_6$-GGOH (orange), $H_8$-GGOH (gray) are shown with signature ions used for structural assignment of products.
Figure 4:
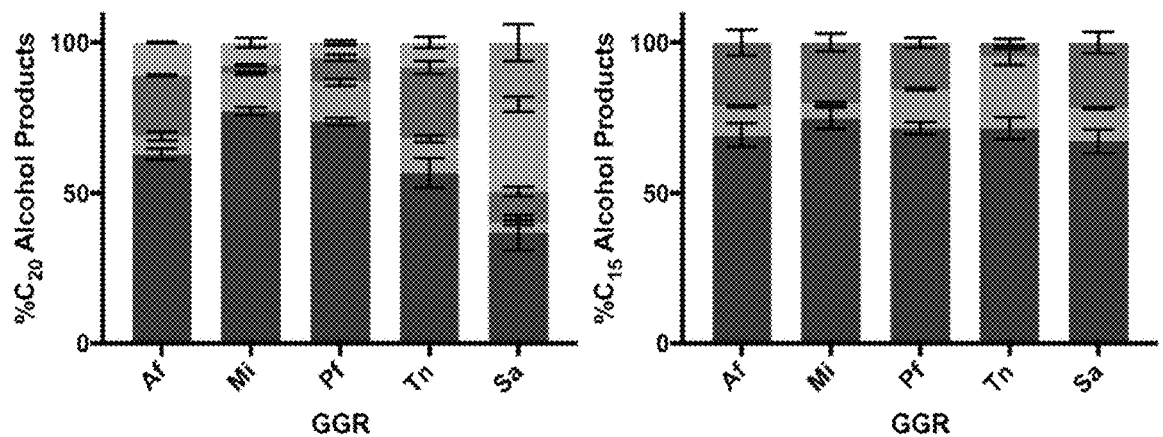
FIG. 4. Endpoint activity profiles for GGR reduction of either GGOH (left) or FOH (right) incubated under standard assay conditions for 1 hr. Product distributions are represented as relative percentages of unreduced substrate (blue), $H_2$-GGOH or $H_2$-FOH (green), $H_4$-GGOH or $H_4$-FOH (red), $H_6$-GGOH or $H_6$-FOH (orange), and $H_8$-GGOH (gray).

Out of 12 purified GGRs, five were discovered to enzymatically reduce geranylgeraniol (GGOH). Neat GGOH substrate eluted at a retention time (RT) of 8.4±0.1 min (FIG. 3B), with a directly proportional TIC response ranging from 0-200 µM (FIG. 10). Upon incubation with any of five putative GGR's isolated from *Archaeoglobus fulgidus* (AfGGR), *Methanocaldococcus infernus* (MiGGR), *Pyrolobus fumarii* (PfGGR), *Thermococcus nautili* (TnGGR), or *Sulfolobus acidocaldarius* (SaGGR), several peaks eluting earlier than 8.4 minutes were observed (FIG. 3B). These peaks were assigned to structures of $H_2$-GGOH (RT=8.1±0.1 min), $H_4$-GGOH (RT=7.9±0.1 min), and $H_6$-GGOH (RT=7.7±0.1 min). Moreover, as protein concentration was increased, substrate consumption accelerated (FIG. 11) with a concomitant increase in formation of the various product peaks (data not showed), confirming enhanced isoprenoid reduction in presence of higher concentration of enzymes. Out of all enzymes tested, SaGGR was the most active toward GGOH, with a specific activity of at least 50±10 nmol terpenoids reduced per milligram of enzyme per hour (FIG. 4 and Table 2). Typically, 70% of the initial GGOH would be recovered regardless of the varying amounts of reduced product formed. Hence, we assumed that all unrecovered substrate was unreduced, and the turnover numbers presented herein most likely represent a lower bound for reductase activity.

TABLE 2

Specific activities of various enzymatic GGR reduction on geranylgeraniol and farnesol.

| | $^a$GGOH | $^a$FOH |
|---|---|---|
| Af GGR | 22 (5) | 9 (2) |
| MiGGR | 10 (2) | 8 (2) |
| PfGGR | 9 (1) | 7 (1) |
| TnGGR | 20 (5) | 5 (1) |
| SaGGR | 50 (10) | 8 (1) |

$^a$Units reported in nmol terpene units reduced $mg^{-1}$ enzyme $hr^{-1}$.

The $H_2$-GGOH and $H_4$-GGOH peaks have respective prevalent ion abundances at 261 and 263 m/z, which can be achieved by loss of a 31 Da [M-$CH_2$OH] fragment during ionization and subsequent formation of a resonance-stabilized singly—or doubly—reduced geranylgeranyl fragment. Such fragments most likely originate from the prenyl units distal from the alcohol group being reduced first, in accordance with previous mechanistic proposals performed using various substrates on a variety of GGR's [29, 32, 33]. Moreover, the $H_6$-GGOH peak matches with a phytol peak from the NIST database with >90% probability, further reinforcing a mechanism of serial reduction of substrate beginning with the 6-prenyl group. Interestingly, several GGR's exhibit unknown side-products, with the most prevalent behavior observed between the $H_2$-GGOH and $H_4$-GGOH peaks in *Pyrolobus fumarii* GGR (RT=8.0 mins) (FIG. 3B). This peak contains aberrant patterns for prenyl units within m/z window of 50-100, and we suggest these are $H_4$-GGOH regioisomers in which one or both internal prenyl units are reduced first, which was suggested from the NIST database with >80% probability (FIG. 12).

Of most noteworthy interest is the product eluted at 7.5±0.1 min RT from assays containing GGR's from *Sulfolobus acidocaldarius* (FIG. 3B). The mass spectra are matched against the 3,7,11,15-teramethylhexadecan-1-ol compound, a complete hydrogenation product of GGOH, in the NIST database with >88% probability. SaGGR, among others, has been demonstrated to reduce 3 out of 4 prenyl units of GGPP at best as observed in this work and others [29, 33]. Because a complete reduction is not observed in isoprenoid pyrophosphate substrates (FIG. 5) but is observed in the isoprenoid alcohol (FIG. 3B), it seems that the absence of phosphate groups might facilitate enhanced diffusion of the α-prenyl group to the flavin reducing site in the alcohol substrates, leading to a fully reduced product. To our knowledge, this is the first evidence of any nonnative isoprenoid substrate undergoing full reduction by any known or putative GGR enzyme.

Figure 6:
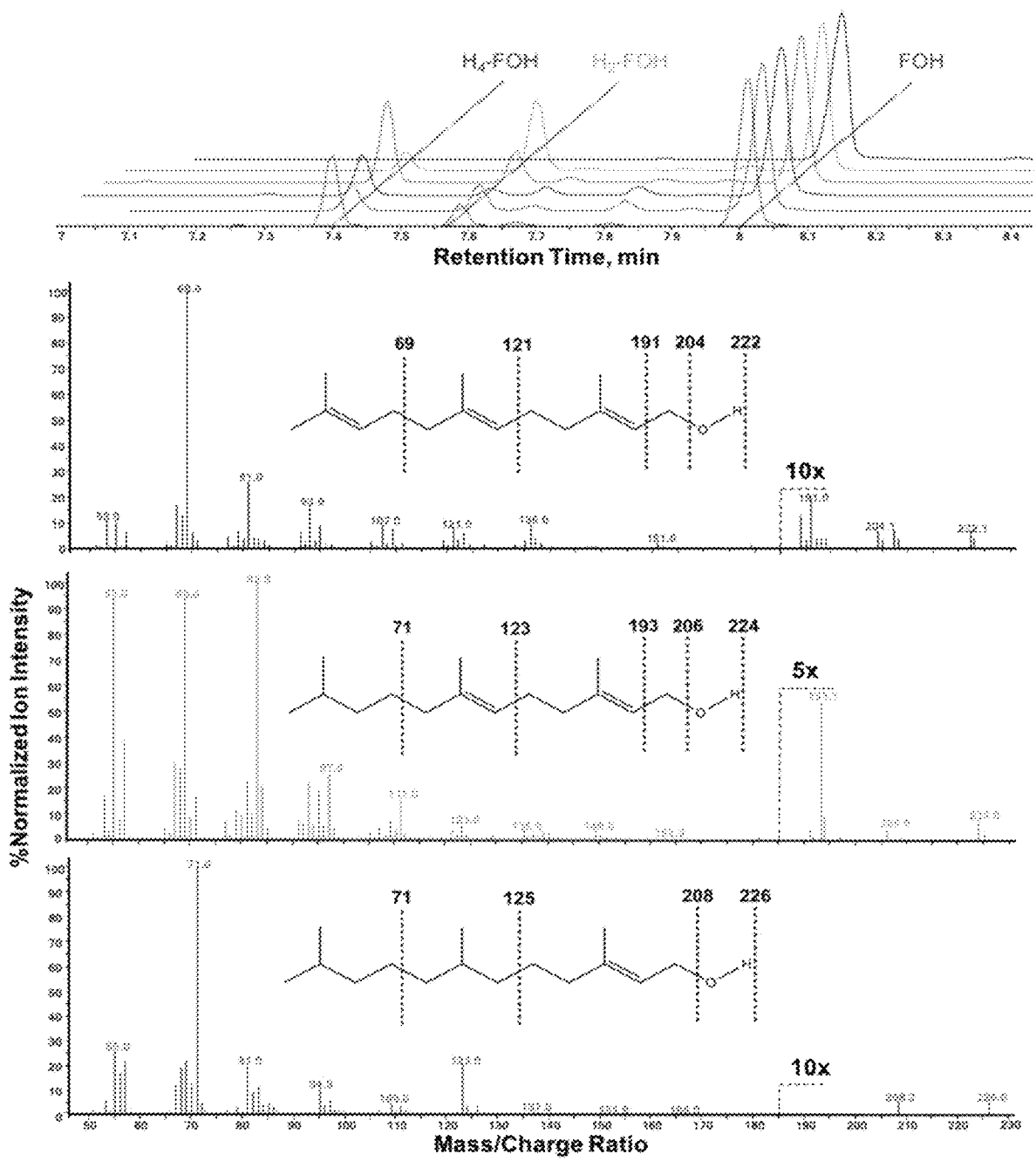
FIG. 6. (Top) Normalized TIC profiles of five putative GGRs (Af, red; Mi, green; Pf, blue; Sa, magenta; Tn, orange; No enzyme, black) found to reduce FOH (RT=8.00 min) to $H_2$-FOH (RT=7.58 min) or $H_4$-FOH (RT=7.40 min) upon 1 hr incubation under standard assay conditions. All peaks elute with a retention time error of ±0.05 minutes. (Bottom) The associated mass spectra for each peak are shown with signature molecular ions for structural assignment of products.

Similarities in reducing activity were also prevalent using farnesol as a substrate. The unreduced FOH substrate eluted with a RT of 8.0±0.1 min, with the putative singly- ($H_2$-FOH) and doubly-reduced ($H_4$-FOH) farnesol eluting at 7.6±0.1 min and 7.4±0.1 min, respectively (FIG. 6). Farnesol ionization was also directly proportional to concentration ranging from 0-200 μM (FIG. 10). The accompanying mass spectrum for $H_2$-FOH reveals a similar ionization pattern to that observed in $H_2$-GGOH via the prevalence of a strong 193 m/z peak. This parallels the $H_2$-GGOH peak pattern containing one less prenyl group (m/z=70 Da). This suggests that the terminal isoprenoid unit is also reduced first in farnesol, conserving the enzymatic reduction mechanism regardless of substrate. The $H_4$-FOH peak at 7.4 min more closely resembles the $H_6$-GGOH peak, with identical peak groupings near the 71, 81, and 123 m/z parent fragments.

Unlike GGOH, all GGRs appeared to have similar levels of FOH products under standard assay conditions, exhibiting an average specific activity of 7±2 nmol terpenoid groups reduced $mg^{-1}$ enzyme $hr^{-1}$ (FIG. 4 and Table 2). Notably, reduction patterns in TnGGR on FOH differ slightly from the other GGRs under standard assay conditions, as its major product is $H_2$-FOH instead of $H_4$-FOH (FIG. 4). No fully reduced farnesol peaks were observed under standard assay conditions nor at enzyme concentrations as high as 150 μM at pH 7.4. However, SaGGR generated a modest amount of $H_6$-FOH when incubated under the enzyme's optimal conditions at 50° C. and pH 5.5[33] (FIG. 13).

Compared to GGOH, emergent side products are less prevalent in the farnesol TIC's. Whereas multiple peaks were observed between the singly- and doubly-reduced GGOH (FIG. 3B), a single prevalent peak at 7.8 minutes elutes between FOH and $H_2$-FOH, mainly observed when incubated in the presence of Pf and MiGGR (FIG. 6). The associated mass spectrum is tentatively assigned to a regioisomer of $H_2$-FOH where the middle prenyl unit is reduced first (FIG. 14). The spectrum matches the NIST database for (E)-3,7,11-trimethyldodeca-2,10-dien-1-ol with a probability of 85% (FIG. 14). Many of the aberrant mass groupings between 50-100 m/z (FIG. 14) parallel those observed in the GGOH reaction incubated with PfGGR (FIG. 12). However, the 7.8 minutes peak does not contain the m/z 193 ion. This ion could be formed by cyclization of a [M-$CH_2OH$] fragment containing a reduced terminal prenyl group and is absent in products where the middle group is reduced first due structural rigidity associated with the remnant α- and γ-prenyl groups. This observation, coupled with the aberrant TIC product profile observed with GGOH, suggests a promiscuous mechanism in which PfGGR has been observed to reduce prenyl monomers out of order with respect to their polymeric structural order.

In Vitro Activity with Isoprenoid Pyrophosphates.

The twelve soluble GGRs successfully purified were tested for reductase activity on FPP and GGPP, and products were detected by LC-MS-TOF. Both farnesyl pyrophosphate (FPP, m/z=381.123±0.001 Da) and geranylgeranyl pyrophosphate (GGPP, m/z=449.183±0.002 Da) standards eluted with a retention time of 1.70±0.05 min (FIG. 5); both substrates produced linear standard curves over a concentration range of 0-120 μM (FIG. 15). When incubated with GGR under standard assay conditions, reduced isoprenoid products were observed to co-elute with fully oxidized substrate under isocratic LC conditions. Therefore, only normalized LC-MS-TOF spectra were utilized to distinguish the relative levels reduced and oxidized compounds that co-elute after incubating with GGR's isolated from various species.

Figure 5:
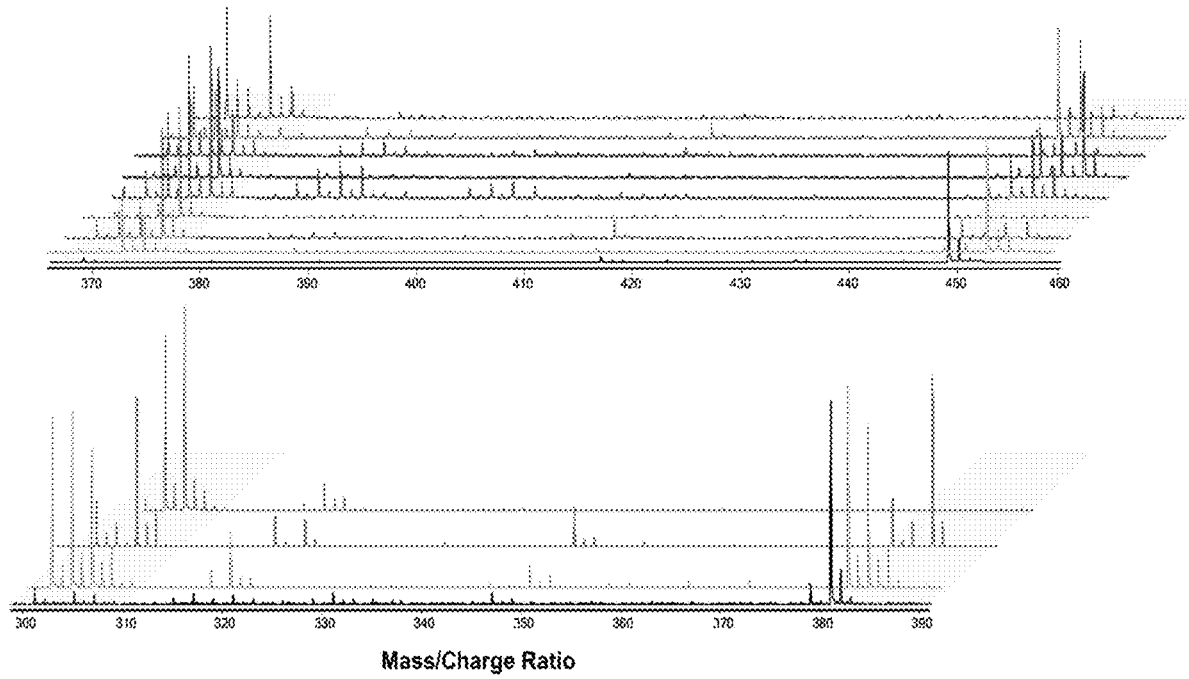
FIG. 5. (Top) Normalized MS-TOF spectra for eight putative GGRs (No Enzyme, black; Tn, orange; Pf, green; Sa, magenta; Af, red; Mi, blue; Sc, purple; Ta, cyan; Ma, brown) found to reduce GGPP (m/z 449-457, highlighted in gray) or GGP (m/z 369-377, highlighted in gray). (Bottom) Normalized MS-TOF spectra for the three putative GGRs (Tn, orange; Pf, green; Sa, magenta) found to reduce FPP (m/z 381-387, highlighted in gray) or FP (m/z: 301-307, highlighted in gray). Reduced products are signified by abundances present at increases of ca. 2 Da from GGPP, GGP, FPP, or FP.

Interestingly, all proteins in this study discovered to enzymatically reduce prenyl pyrophosphates revealed co-eluting side products indicative of substrate or product hydrolysis of one phosphate moiety (FIG. 5). Increased abundances of farnesyl monophosphate (FP, m/z=301.177±0.001 Da) or geranylgeranyl monophosphate (GGP, m/z=369.213±0.003 Da) only emerged when incubated with enzyme; minimal hydrolysis was observed in GGPP or FPP standards and relative GGPP/GGP and FPP/FP ratios remained constant as a function of time in negative controls ran without enzyme (FIG. 16). Structural studies of SaGGR crystallized with GGPP revealed three distinct substrate binding modes with varying degrees of phosphorylation within each binding position [33]. Within the catalytically relevant binding mode, both phosphate moieties are resolved. In the other two binding modes, however, either one or zero phosphate groups were structurally resolved. This was attributed to dephosphorylation during the crystallization process [33]. Herein, we observed a time-dependent emergence of hydrolyzed monophosphate products via LC-MS-TOF, yet it still requires further characterization how the enzyme facilitates this phenomenon while conducting substrate reduction.

Reductase activity on FPP and GGPP varied from what was observed on alcohol substrates (FIG. 7). Indeed, none of the GGRs tested could significantly reduce all vinyl groups within FPP or GGPP even when GGRs were incubated under the optimal condition for enzyme activity (at 50° C. and pH 5.5) (data not shown). Out of the five GGRs found to reduce FOH, only PfGGR, TnGGR, and SaGGR could reduce FPP. On the other hand, three GGRs isolated from *Streptomyces coelicolor* (ScGGR), *Methanosarcina acetivorans* (MaGGR), and *Thermoplasma acidophilum* (TaGGR) were found to reduce GGPP along with the five GGRs demonstrating reductase activity toward GGOH. Most GGRs that have been isolated thus far, were from archaea; to our knowledge, ScGGR is the first bacterial GGR demonstrated to reduce GGPP. Due to unexpected hydrolysis of one phosphate moiety under standard assay conditions, specific activities for reduction were not quantified for any GGR. However, relative reductase activities can be gleaned by quantifying the proportion of reduced and unreduced compounds present within intact or hydrolyzed mass groupings (FIG. 7). For example, the relative ion intensities of each singly-reduced product ($H_2$-FPP or $H_2$-FP) present is normalized to the sum of FPP, $H_2$-FPP, $H_4$-FPP, $H_6$-FPP, FP, $H_2$-FP, $H_4$-FP, and $H_6$-FP extracted ion intensities.

Interestingly, all GGR's revealed a larger proportion of reduced products present as hydrolyzed moieties than non-hydrolyzed moieties (FIG. 7). To discern a correlation between enzymatic phosphate hydrolysis and enzymatic reduction of prenyl monophosphates, we assayed PfGGR and SaGGR as a function of time, as these enzymes are representative of low and high amounts of monophosphate found after standard assay incubation, respectively (FIG. 16). Indeed, substrate hydrolysis appears to react as a first-order exponential process which occurs more quickly in SaGGR than for PfGGR (FIG. 17). Moreover, the relative abundances of reduced monophosphate products increase over time in both assays, indicating that most GGR's can still reduce FP or GGP as a substrate during substrate hydrolysis (FIG. 18). Such an inference is reasonable considering many GGR's assayed enzymatically reduce terpenoid alcohols and pyrophosphates.

Promiscuous hydrolysis complicates any interpretations regarding which enzymes are most active toward a given substrate due to the inability to quantify the MS response of terpenoid phosphates. However, it can be inferred that all GGRs can reduce between 5-10 nmol prenyl groups of FPP or GGPP $mg^{-1}$ enzyme $hr^{-1}$. The turnover number would be modestly elevated for GGPP reduction, as all $C_{20}$ species are extracted as some partially reduced product within error after 1 hr. Such turnover numbers are in line with other reports on GGR's with a variety of substrates [32, 33].
Structural Insights and Mechanistic Implications.

Several synthetic approaches are currently being explored to perform selective hydrogenation on a few substrates [34-36]. Biological systems such as enoyl-CoA reductase and Old Yellow Enzyme exhibit a similar oxidoreductase activity to GGR, yet benefit from active sites that enhance the electron-withdrawing nature of α,β-unsaturated carbonyl substrates [17-20]. Patented ene-reductases utilizing Old Yellow Enzyme as a scaffold enhance reductase activity on a variety of substrates by evolving active sites complementary to a variety of electron withdrawing groups among a diverse variety of α,β-unsaturated substrates [37]. However, an evolved GGR active site designed for isoprenoid reduction would probably require significant divergence from these scaffolds since they do not utilize electron-withdrawing activation for alkene reduction [30].

Of the eight proteins that were identified as GGRs active toward terpenoid alcohols and/or terpenoid pyrophosphates, five (Sa-, Pf-, Af-, Mi-, and TnGGRs) were isolated from archaeal organisms that optimally thrive under hyperthermophilic conditions (i.e., T≥80° C.). SaGGR, TaGGR, and AfGGR have been identified to reduce various large intermediates (i.e., larger than 20 carbons) associated with archaeal lipid biosynthesis, with GGPP or GGOH serving as the smallest substrates known to undergo prenyl reduction [27, 29, 32]. In this study, we have significantly expanded the known GGR substrate activity profiles, demonstrating multiple prenyl group reduction in GGOH and FOH within all five hyperthermophilic GGRs.

In addition to the five GGRs active on alcohols, TaGGR, MaGGR, and ScGGR also sufficiently reduced GGPP or GGP (FIGS. 5 and 7). However, only PfGGR, SaGGR, and TnGGR were found to reduce the smaller FPP or FP substrates. Because the relative amount of $H_2$-, $H_4$-, and $H_6$-GGOH increase in relative abundances within the monophosphate mass groupings relative to the pyrophosphate mass groupings, it can be inferred that prenyl monophosphates are also substrates reduced by several GGRs (FIG. 18). This seems suitable given the ability of several GGRs to reduce prenyl alcohols.

A structural alignment of all eight active GGRs reveals very little commonalities among all protein sequences with known crystal structures: SaGGR and TaGGR, with PfGGR ca. 46% identical to SaGGR and MaGGR, MiGGR, and AfGGR ca. 40-46% identical to TaGGR (FIG. 8). SaGGR and TaGGR contain three domains: an FAD binding domain, a catalytic domain, and a C-terminal domain [29, 30]. While sequence identities remain low among all demonstrably active GGRs, certain key structural motifs remain conserved within their predicted FAD binding domains and catalytic domains. Of the two known crystal structures of active GGRs, both contain an active site cysteine (Cys47 in SaGGR; Cys45 in TaGGR) thought to serve as a critical redox modulator within the active site during reduction. All GGRs shown to reduce either isoprenoid alcohols or pyrophosphates contain this critical cysteine within their cofactor binding domains, suggestive of a conserved electron transfer mechanism. In addition, all sequences predicted catalytic domains contain the YXWXFP (SaGGR residues 215-220) and GGG motifs (SaGGR residues 298-300) believed to modulate substrate interactions and assist in substrate diffusion through the reduction center.

Protein structures of aligned sequences were predicted using either SaGGR or TaGGR as a template. While there is a fair amount of expected structural divergence among the structures' surfaces, a comparison of the active sites reveals a fair degree of similarity in topology (FIG. 9). However, some of the structural motifs strictly conserved among all archaeal GGR's exhibit significant divergence within ScGGR, the only known GGR to be isolated from a bacterial organism. While all archaeal GGRs studied in this work possess a $YXWXFPX_7$ GXG motif (SEQ ID NO:9) or $YXWXFPX_8$GXG motif (SEQ ID NO:12), the terminal glycine is mutated to isoleucine in ScGGR. Even more interestingly, the GGG motif has significantly diverged to REG in ScGGR. In several GGRs from photosynthetic organisms with demonstrated capability to reduce prenylated chlorophyll, *Rhodobacter sphaeroides*, *Synechocystis* sp. PCC 6803, and *Arabidopsis thaliana*, this motif was found to be GEG [26, 38, 39]. It seems that non-archaeal GGRs utilize preferentially charged residues within this critical catalytic region to either enhance polar interactions on prenylated substrates containing polar groups or to introduce critical hydrogen-bonding interactions that help maintain the integrity of the substrate tunnel during reduction (FIG. 9).

Mechanistic interpretations from other groups propose that the prenyl group closest to the pyrophosphate moiety (α-prenyl group) remains oxidized in GGPP and FPP. This observation additionally applies to their monophosphate counterparts in this work, FP and GGP. All enzymes tested to date seem to conserve this characteristic of avoiding reduction at the α-position on phosphate intermediates, aligning with current paradigms that auxiliary prenyl reductases are responsible for reducing this group in archaea and eukaryotes [40].

To our knowledge, full isoprenoid reduction by GGR has only been observed with its natural $C_{40}$ isoprenoid substrate DGGGP. In this work, we observed full reduction for the first time on smaller (i.e., $C_{20}$ or $C_{15}$) isoprenoid alcohol substrates, namely GGOH and FOH with SaGGR (FIGS. 3, 4, 6, FIG. 13). Interestingly, the absence of phosphate groups appears to assist in full substrate reduction. Analysis of the catalytically relevant binding mode of GGPP in SaGGR reveals that binding site residues His55 and Asn90 could provide hydrogen bonding interactions with phosphate moieties that could prevent the α-prenyl group from being reduced [33]. Alcohol substrates may not interact as strongly with these residues, facilitating a degree of full reduction unobserved in pyrophosphate substrates. Why some enzymes reduce isoprenoid alcohol and pyrophosphate substrates while others only reduce isoprenoid pyrophosphates requires further structural characterization.

Improved Activity of GGR by Rational Design

Sa-GGR is less efficient on short chain isoprenoid and has been demonstrated to have a temperature optimum at 50° C. and pH 5.5 in vitro. However, utilizing SaGGR in industrial processes require that its activity is optimized at neutral pH and at lower temperatures (i.e., 30-37° C.). To investigate the involvement of amino acids involved in short chain substrate binding, to investigate the possibility to improve the activity on short chain and based on the available SaGGR and TaGGR crystal structures, some amino acids located in the binding pocket, at the end of the substrate were tested by alanine scan (FIGS. 19A and 19B). Two mutations (L377H and E209A) could increase the activity of the enzyme on FPP (FIG. 19B). The mutation L377H was showed in the past to be responsible of enhancing the reduction rate of SaGGR on GGPP, this mutation is also improving the activity on FPP. The mutation of E209A was shown for the first time to improve activity on FPP.

Other mutations in the active site of SaGGR has shown considerable promise for partial substrate reduction via kinetic control. For example, G298 is a conserved residue among known GGR. The G298A mutant significantly inhibits serial reduction of FPP, forming singly-reduced H2-FPP as final product (FIGS. 20A and 20B).

Activity of Other GGRs

A large set of GGRs isolated from various organisms including archaea, bacteria and cyanobacteria have been tested on various substrates. Table 5 summarizes the activity of the heterologous enzymes on various substrates.

potential suitability for integration into *S. cerevisiae* or *E. coli*. Moreover, the confirmation of reduction on $C_{15}$ isoprenoids instantly expands the metabolic engineering potential for organisms producing sterol and squalene-derived isoprenoids. There are still unresolved issues to address for a direct application of these newly discovered GGR's to manufacture reduced isoprenoids. For example, more engineering will be needed on these enzymes to avoid enzymatic hydrolysis of isoprenoid pyrophosphates and to improve their activities especially at mesophilic condition. Nonetheless, this study demonstrated significant substrate promiscuity among these GGRs and could potentially open new pathways for isoprenoid-based polymers, chemicals, or biofuels by allowing for upstream reduction of various intermediates within the heavily utilized MEV or DXP terpene biosynthesis pathways.

TABLE 5

Summary of activity of various GGR on various substrates.

| GGR name | Organism | Kingdom | GPP (C10) reduction | FPP (C15) reduction | GGPP (C20) reduction | Geraniol (C10) reduction | Farnesol (C15) reduction | Farnesol (C15)-full reduction | Geranylgeraniol (C20) reduction |
|---|---|---|---|---|---|---|---|---|---|
| Af1-GGR | *Archaeoglobus fulgidus* | archaea | nt | − | + | + | + | − | + |
| Cn-GGR | *Candidatus Nitrosopumilus* | archaea | nt | − | − | nt | − | − | − |
| Ma1-GGR | *Methanosarcina acetivorans* | archaea | nt | − | + | nt | − | − | − |
| Mb-GGR | *Methanococcoides burtonii* | archaea | nt | − | − | nt | − | − | − |
| Mi-GGR | *Methanocaldococcus infernus* | archaea | nt | − | + | + | + | − | + |
| Mr2-GGR | *Methanobrevibacter ruminantium* | archaea | nt | − | − | nt | − | − | − |
| Pf-GGR | *Pyrolobus fumarii* | archaea | nt | + | + | − | + | + | + |
| Sa-GGR | *Sulfolobus acidocaldarius* | archaea | + | + | + | − | + | + | + |
| Sc1-GGR | *Streptomyces coelicolor* | bacteria | nt | − | + | nt | − | − | − |
| Syn-GGR | *Synechocystis species* | Cyanobacteria | nt | − | − | nt | − | − | − |
| Ta-GGR | *Thermoplasma acidophilum* | archaea | nt | − | + | − | − | − | − |
| Tn-GGR | *Thermococcus nautili* | archaea | nt | + | + | − | + | − | + |

Abbreviations: nt, + and ++ mean reciprocally: not tested, activity detected, and activity higher than for other GGRs.

CONCLUSIONS

In this study, we have significantly expanded the possible activities among proteins demonstrated to enzymatically reduce prenyl pyrophosphates or prenyl alcohols. We have demonstrated 1) the discovery of four novel protein sequences (PfGGR, MiGGR, ScGGR, and TnGGR) that have confirmed GGR activity in vitro in addition to expanded observed activities among previously characterized GGRs; 2) that several GGR's can reduce $C_{15}$ terpenoid substrates, substrates smaller than reported substrates for GGR activity; 3) the complete reduction of double bonds on any $C_{20}$ or $C_{15}$ isoprenoid using SaGGR; 4) reductase activity on terpenoid monophosphates formed from hydrolysis of pyrophosphate substrates under reducing conditions in vitro; 5) the quantification of reductase specific activity on terpenoid alcohols; and 6) the confirmed isoprenoid reductase activity of the second known non-archaeal enzyme, as observed in the GGR isolated from *Streptomyces coelicolor*.

This demonstration of protein expression and reductase activity at neutral pH and low temperature highlights their

METHODS

All chemicals and reagent were purchased from Sigma-Aldrich (St. Louis, MO), unless otherwise indicated. (E,E)-Farnesol was purchased from Alfa Aesar (Haverhill, MA) and glycerol from VWR (Westchester, PA). Solvents for high performance liquid chromatography (HPLC) were purchased from HoneyWell Burdick and Jackson (Morristown, NJ) and were of HPLC grade or higher. Ammonium carbonate (30-33% $NH_3$ basis) was purchased from Fluka Analytical Sigma-Aldrich (St. Louis, MO). Restriction enzymes and polymerases were purchased from New England Biolabs (Ipswich, MA).

Sequence Analysis and GGR Homology.

Multiple sequence alignments for potential GGR hits were generated using MUSCLE v. 3.8.31 and visualized using Geneious 7.0.6 [41, 42]. Sequences were curated manually, and phylogeny trees were computed using the maximum likelihood tree within the RAxML Software package, v. 8.1.24 under the LG plus gamma model of evolution (PROTGAMMALG in the RAxML model section) [43]. The MRE-based bootstrapping criterion were automatically determined for phylogeny tree construction. Annotation of the tree was performed in Itol [44]. After verification of GGR activity, the active enzymes underwent a second multiple sequence alignment and modeled for their predicted protein structures via SWISS-MODEL-PDB using either SaGGR or TaGGR as templates [45]. Active site geometries and local structures for all proteins were visualized using Chimera [46].

Plasmid Synthesis and Transformation.

The gene encoding SaGGR was amplified by PCR from the pSKB3-SaGGR plasmid using the forward (5'-GATATA-CATATGAAGGAACTTAAATATGACGTTCTG-3') (SEQ ID NO:10) and reverse (5'-GTCGACGGAGCTCGAACT-TAAACTTTTGTTAAACTCTGTTAGAAC-3') (SEQ ID NO:11) primers synthesized by Integrated DNA Technologies [33]. The PCR fragment was digested at the NdeI and SacI restriction sites and cloned into the pET-24a vector using the rapid DNA ligation kit (Roche). All other putative GGR genes were synthesized by GeneWiz (N.J., USA) and similarly cloned into the pET-24a vector at the same restriction sites. All gene constructs are available through the JBEI registry at the website for: public-registry.jbei.org (Table 1 and Table 4).

TABLE 4

Table of plasmids used in the present study. The strains harboring individual plasmid are available at the public registry of the Joint BioEnergy Institute (website for: public-registry.jbei.org/) under the ID's listed in the righthand column.

| Plasmid Name | Organism | Ref. in JBEI registry |
| --- | --- | --- |
| pET-AfGGR | Archaeoglobus fulgidus #1 | JBx_095992 |
| pET-Af2GGR | Archaeoglobus fulgidus #2 | JBx_095994 |
| pET-AtGGR | Arabidopsis thaliana | JBx_095980 |
| pET-CnGGR | Candidatus Nitrosopumilus | JBx_095996 |
| pET-CtGGR | Corynebacterium terpenotabidum | JBx_095998 |
| pET-GpGGR | Gordonia polyisoprenivorans | JBx_096000 |
| pET-HcGGR | Halorubrum californiensis | JBx_096002 |
| pET-HlGGR | Halostagnicola larsenii X | JBx_096004 |
| pET-HsGGR | Haloterrigena salina | JBx_096006 |
| pET-Hv1GGR | Haloferax volcanii #1 | JBx_096008 |
| pET-Hv2GGR | Haloferax volcanii #2 | JBx_096010 |
| pET-Ma1GGR | Methanosarcina acetivorans #1 | JBx_096050 |
| pET-Ma2GGR | Methanosarcina acetivorans #2 | JBx_096012 |
| pET-Ma3GGR | Methanosarcina acetivorans #3 | JBx_096014 |
| pET-MbGGR | Methanococcoides burtonii | JBx_096020 |
| pET-McGGR | Metallosphaera cuprina | JBx_096022 |
| pET-MiGGR | Methanocaldococcus infernus | JBx_096024 |
| pET-MmGGR | Methanococcus maripaludis | JBx_096026 |
| pET-Mr1GGR | Methanobrevibacter ruminantium #1 | JBx_096028 |
| pET-Mr2GGR | Methanobrevibacter ruminantium #2 | JBx_096030 |

TABLE 1

Table of proteins tested for potential enzymatic isoprenoid reductase activity. The molecular weight of the enzymes includes the N-terminal His tag sequence.

| GGR name | Organism | Type | INTERPRO Number | molecular weight (kDa) |
| --- | --- | --- | --- | --- |
| Af1GGR | Archaeoglobus fulgidus #1 | archaea | >A0A075WA57 | 44 |
| Af2GGR | Archaeoglobus fulgidus #2 | archaea | >A0A075WDX8 | 42 |
| AtGGR | Arabidopsis thaliana | plant | >Q9CA67 | 49 |
| CnGGR | Candidatus Nitrosopumilus | archaea | >K0BBV2 | 47 |
| CtGGR | Corynebacterium terpenotabidum | bacteria | >S4XGC5 | 49 |
| GpGGR | Gordonia polyisoprenivorans | bacteria | >H6N2C4 | 46 |
| HcGGR | Halorubrum californiensis | archaea | >M0EA67 | 41 |
| HlGGR | Halostagnicola larsenii X | archaea | >W0JLI3 | 52 |
| HsGGR | Haloterrigena salina | archaea | >M0BU08 | 53 |
| Hv1GGR | Haloferax volcanii #1 | archaea | >D4GXW9 | 53 |
| Hv2GGR | Haloferax volcanii #2 | archaea | >D4H022 | 41 |
| Ma1GGR | Methanosarcina acetivorans #1 | archaea | >Q8TQQ6 | 46 |
| Ma2GGR | Methanosarcina acetivorans #2 | archaea | >Q8TLY0 | 47 |
| Ma3GGR | Methanosarcina acetivorans #3 | archaea | >Q8TSV3 | 45 |
| MbGGR | Methanococcoides burtonii | archaea | >Q12WF0 | 46 |
| McGGR | Metallosphaera cuprina | archaea | >F4FYK4 | 53 |
| MiGGR | Methanocaldococcus infernus | archaea | >D5VQY0 | 45 |
| MmGGR | Methanococcus maripaludis | archaea | >Q6LXX0 | 45 |
| Mr1GGR | Methanobrevibacter ruminantium #1 | archaea | >D3E3T0 | 45 |
| Mr2GGR | Methanobrevibacter ruminantium #2 | archaea | >D3E430 | 51 |
| NgGGR | Nitrososphaera gargensis | archaea | >K0IKB9 | 43 |
| PcfGGR | Pyrococcus furiosus | archaea | >Q8U3L2 | 43 |
| PfGGR | Pyrolobus fumarii | archaea | >G0EHJ8 | 53 |
| SaGGR | Sulfolobus acidocaldarius | archaea | >M1I414 | 52 |
| ScGGR | Streptomyces coelicolor #1 | bacteria | >Q9K426 | 47 |
| SeGGR | Synechococcus elongatus #1 | cyanobacteria | >Q31QX9 | 43 |
| SynGGR | Synechocystis species | cyanobacteria | >L8ATV2 | 47 |
| TaGGR | Thermoplasma acidophilum #1 | archaea | >Q9HKS9 | 45 |
| TnGGR | Thermococcus nautili | archaea | >W8NRH6 | 46 |
| Tr1GGR | Thermocrinis ruber #1 | bacteria | >W0DGJ3 | 41 |
| Tr2GGR | Thermocrinis ruber #2 | bacteria | >W0DID8 | 42 |

TABLE 4-continued

Table of plasmids used in the present study. The strains harboring individual plasmid are available at the public registry of the Joint BioEnergy Institute (website for: public-registry.jbei.org/) under the ID's listed in the righthand column.

| Plasmid Name | Organism | Ref. in JBEI registry |
| --- | --- | --- |
| pET-NgGGR | Nitrososphaera gargensis | JBx_096032 |
| pET-PcfGGR | Pyrococcus furiosus | JBx_096034 |
| pET-PfGGR | Pyrolobus fumarii | JBx_096036 |
| pET-SaGGR | Sulfolobus acidocaldarius | JBx_095970 |
| pET-ScGGR | Streptomyces coelicolor #1 | JBx_096038 |
| pET-SeGGR | Synechococcus elongatus #1 | JBx_096040 |
| pET-SynGGR | Synechocystis species | JBx_096042 |
| pET-TaGGR | Thermoplasma acidophilum #1 | JBx_096052 |
| pET-TnGGR | Thermococcus nautili | JBx_096044 |
| pET-Tr1GGR | Thermocrinis ruber #1 | JBx_096046 |
| pET-Tr2GGR | Thermocrinis ruber #2 | JBx_096048 |

10 ng of each plasmid were transformed by heat shock at 42° C. for 1 min into chemically competent E. coli BL21 cells harboring the pG-KJE8 plasmid encoding DnaK, DnaJ, GrpE, GroES, and GroEL protein chaperones (Takara Bio Inc., Shiga, Japan). Transformed cells were recovered in 1 mL of Lysogeny Broth (LB) medium (VWR) and incubated for 1 hr at 37° C. with shaking at 200 rpm. Following recovery, cells were plated on LB-Agar containing 50 mg/L of kanamycin (VWR) and 30 mg/L of chloramphenicol (VWR), and incubated overnight at 37° C. Select colonies were grown overnight in LB medium containing 50 mg/L of kanamycin and 30 mg/L of chloramphenicol and stored in 20% glycerol (VWR) at −80° C. for future use.

Cell Culture, Protein Expression, and Protein Purification.

Overnight seed cultures of 1 mL each were inoculated into 400 mL of Terrific Broth (TB) medium supplemented with 50 mg/L kanamycin and 30 mg/L chloramphenicol and incubated at 37° C. and 200 rpm. At an $OD_{600}$ of 0.2-0.3, chaperone overexpression was induced with 5 ng/mL tetracycline (VWR) and 2.5 mM arabinose (Sigma-Aldrich). After the $OD_{600}$ reached ≥1.0, GGR expression was induced with 0.1 mM IPTG (VWR) and incubated at 18° C. overnight. Cells were pelleted at 6000×g for ten minutes and immediately lysed using 20 mM phosphate buffer, pH 8.0 containing 1 mg/mL lysozyme, 20 mM imidazole, 200 mM NaCl, and 0.1 mM PMSF protease inhibitor (Sigma-Aldrich). After sonication for 10 minutes, the remaining cell debris was pelleted at 15000×g for 45 minutes.

Protein expression was tested for each construct using SDS-PAGE and Western blot. For SDS-PAGE analysis, protein samples were normalized for concentration using absorbance at 280 nm. Lysates were diluted with 2× SDS loading dye buffer (Life Technologies, CA, USA) containing 10 mM DTT (Sigma-Aldrich) and incubated at 98° C. for 20 min. 10 μL of denatured lysate samples were loaded onto an 8-16% Tris-Glycine-SDS gradient gel (Bio-Rad), and separated using a voltage of 180 V in Tris-Glycine-SDS running buffer (Bio-Rad). Gels were either directly stained using GelCode Blue Safe Protein Stain (Thermo-Fisher) or transferred to a nitrocellulose membrane using the trans-Blot Turbo system (Life Technologies, CA, USA) for analysis by Western blot. Membranes were washed in TBS buffer (50 mM Tris, 150 mM NaCl, pH 7.4) and blocked overnight at 4° C. with 25 mL of 3% BSA in TBS-Tween20 (Sigma-Aldrich). The monoclonal mouse anti-His primary antibody (Sigma-Aldrich) was diluted 5000-fold, and an alkaline phosphatase-conjugated goat anti-mouse secondary antibody was diluted 10,000-fold in TBS-Tween20 containing 1% BSA. Membranes were incubated with antibodies for 1 hour each at room temperature and washed three times in TBS-Tween20 after each antibody incubation. The membrane was then incubated in 10 mL of SigmaFast BCIP/NBT Alkaline Phosphatase detection solution (Sigma-Aldrich) for 10 min.

In order to further characterize those putative GGR's that showed significant protein expression, the cells harboring them were cultured in 400 mL of TB-Kan/Cm media and lysed as previously described. Their respective crude lysates were loaded directly onto a 1 mL HisTrap FastFlow column (GE Healthcare), washed with 10 column volumes of 20 mM phosphate buffer containing 20 mM imidazole and 200 mM NaCl at pH 7.4, then eluted with the same buffer containing 240 mM imidazole. For enzyme kinetics, purified enzymes were buffer exchanged using 20 mM phosphate buffer at pH 7.4 and concentrated to 200-800 μM using 30 KDa molecular weight cutoff spin concentrators (EMD Millipore). Purified proteins were stored in 10% (v:v) glycerol and snap frozen in liquid nitrogen. Protein purity and sizes were verified by SDS-PAGE and protein concentrations were quantified by absorbance at 280 nm using each protein's calculated extinction coefficient via the ExPASY ProtParam tool.

In Vitro Enzyme Kinetics Assays.

Validation of enzymatic substrate reduction was determined by incubating all assays in triplicate for each respective substrate and putative GGR for 1 hour at 37° C. All assays were performed at pH 7.4 in 100 mM sodium phosphate buffer containing 30-150 μM enzyme, 200 μM FAD (Sigma-Aldrich), and 65 mM sodium dithionite (Sigma-Aldrich). Standard assays for alcohol reduction were incubated with 100 μM enzyme and 500 μM (E,E)-farnesol (Alfa-Aesar) or (E,E,E)-geranylgeraniol (Sigma-Aldrich); pyrophosphate assays were performed at 100 μM FPP or GGPP (Sigma-Aldrich). Alcohol-based assays were quenched by liquid extraction using a 3:1 (v:v) LC-grade ethyl acetate solution containing 100 μM dodecanol as a GC internal standard (Sigma-Aldrich). The organic layer was extracted and stored at −20° C. until analysis by GC-MS. Pyrophosphate assays were similarly quenched using LC-grade n-butanol (Sigma-Aldrich) 1:1 (v:v) and centrifuged at 15000×g for 2 minutes. The n-butanol layer was dried for 45 minutes at ambient temperature using a Labconco speedvac, reconstituted in 25 μL of a 62:38 (v:v) acetonitrile/50 mM ammonium carbonate solution, and stored at −20° C. until further analysis by LC-MS-TOF [33]. Characterization of enzymatic hydrolysis of isoprenoid pyrophosphate substrates by SaGGR and PfGGR was performed by quenching the enzyme reactions at 0, 2, 5, 10, 20, 40, and 60 minutes of incubation.

Analysis of Alcohol Reduction by GC-MS.

Product identification and quantification of farnesol and hydrofarnesol derivatives were modified from previous detection methods [47]. All GC-MS analyses were determined using an Agilent 6890 gas chromatography instrument coupled to an Agilent 5973 mass selective detector. 1 μL of extracted samples were injected in splitless mode onto an Agilent CycloSil-B column, with helium used as a carrier gas flowing at 1.0 mL/min. Following injection, the oven was held at 50° C. for 30 seconds, then increased to 175° C. at 35° C./min. Farnesol and hydrofarnesols were resolved by increasing the temperature 4° C./min up to 200° C., then increased to 300° C. at a rate of 35° C./min where it was held for 1.5 minutes. Geranylgeraniol and its hydrogenated derivatives were analyzed using the same injection method. After injection, the oven was held at 50° C. for 30 seconds then increased to 235° C. at 35° C./min. Hydrogeranylgeraniols were separated by increasing the oven temperature 4° C./min to 250° C., then ramped to 300° C. at a rate of 35° C./min where it was held for 1.5 minutes.

The EI-MS detection was initiated after a solvent delay of 5.0 minutes. Detection and classification of hydrofarnesols was performed in scan mode at 9.8 scans/sec ranging from 50-250 m/z in positive ion mode. For geranylgeraniol, the same scan parameters were implemented except for the mass range, which was expanded to 50-300 m/z in positive ion mode. The electron multiplier voltage was set to a gain factor of 1, with the MS ion source and quadrupole set to 230° C. and 150° C., respectively.

Total ion chromatograms (TIC) were integrated using Agilent Technologies Masshunter software, version 6. Product formation was determined from the TIC area for $C_{15}$ or $C_{20}$ alcohol products eluting at each respective retention time. Absolute product concentrations were determined from standard curves (0-200 µM) of either farnesol or geranylgeraniol assuming the TIC area of each reduced product ionizes with an equivalent efficiency to that of the unreduced substrate (FIG. 10). Subsequently, enzyme turnover numbers for isoprenoid reduction were calculated as the total number of nanomoles of prenyl units reduced per milligram of enzyme in 1 hr.

Analysis of Pyrophosphate Reduction by LC-MS-TOF.

The separation of FPP, GGPP, and their reduced forms was conducted on a ZIC-pHILIC column (150 mm length, 2.1 mm internal diameter, and 5 µm particle size, Merck) using an Agilent Technologies 1200 Series Rapid Resolution high performance liquid chromatography (HPLC) system. Solvents for HPLC were purchased from HoneyWell and were of HPLC grade or higher. The mobile phases used for this analysis were A) 50 mM ammonium carbonate (Fluka, 30-33% $NH_3$ basis) in water and B) acetonitrile. Analytes were eluted isocratically with a mobile phase composition of 62% B at a flow rate of 0.2 mL/min. The total run time of the method was 6.5 min. The temperature of the sample tray was maintained at 6° C. using an Agilent FC/ALS Thermostat. The column compartment was set to 40° C. A sample injection volume of 2 µL was used throughout [33].

The HPLC system was coupled to an Agilent Technologies 6210 time-of-flight mass spectrometer (LC-TOF-MS) by a ⅓post-column split. Contact between both instrument set-ups was established using a LAN card in order to trigger the MS into operation upon the initiation of a run cycle from the MassHunter workstation (Agilent Technologies). Electrospray ionization (ESI) was conducted in the negative ion mode and a capillary voltage of −3500 V was utilized. MS experiments were carried out in full scan mode, at 0.86 spectra/second for the detection of [M-H]⁻ ions. The instrument was tuned for a range of 50-1700 m/z. Prior to LC-TOF-MS analysis, the TOF-MS was calibrated via an ESI-L low concentration tuning mix (Agilent Technologies).

Data acquisition and processing were performed by the Agilent Technologies MassHunter software package. Product formation was determined using extracted ion chromatogram abundances (±0.02 Da) for each molecule's [M-H]⁻ mass (Table 4). Substrate and product hydrolysis of SaGGR and PfGGR was characterized as a function of time by measuring the relative ratios of prenyl pyrophosphates (FPP/GGPP and reduced products) and monophosphates (FP/GGP and reduced products) at quenched fractions collected at 0, 2, 5, 10, 20, 40, and 60 minutes. Relative reductase reactivity among GGRs was determined by measuring the fractional abundance of singly-, doubly-, or triply-reduced products to the total ion abundance present for intact and hydrolyzed moieties [33]. Integrated areas for hydrolyzed monophosphate products were assumed to have the same ionization intensities as their pyrophosphate counterparts, as determined by their standard curves measured from 0-120 µM (FIG. 15).

LIST OF ABBREVIATIONS

GPP, geranyl pyrophosphate; FPP, farnesyl pyrophosphate; GGPP, geranylgeranyl pyrophosphate; FOH, farnesol; GGOH, geranylgeraniol; GGR, geranylgeranyl reductase; LC-MS, Liquid chromatography-Mass Spectrometry; TOF, Time of Flight; GC-MS, Gas Chromatography-Mass Spectrometry; TIC, Total Ion Chromatogram.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A method for reducing geranyl pyrophosphate (GPP) or geraniol comprising: (a) providing a genetically modified host cell comprising a nucleic acid encoding a polypeptide operatively linked to a promoter, wherein the polypeptide has geranylgeranyl reductase (GGR) enzymatic activity and comprises at least 95% identity to one of SEQ ID NOs: 1-8, and SEQ ID NO:9 or SEQ ID NO:12, and a glycine at position 12, a glycine at position 14, a glycine at position 17, an alanine at position 21, a glycine at position 28, a cysteine at position 47, an alanine at position 109, a glycine at position 113, an alanine at position 156, a glycine at position 158, a glycine at position 287, an aspartate at position 288, a proline at position 295, a glycine at position 300, an alanine at position 304, and an alanine at position 311, wherein (i) the polypeptide is heterologous to the host cell or (ii) the nucleic acid encoding the polypeptide is not operatively linked to the promoter in nature, or a culture comprising the genetically modified host cell, (b) culturing the genetically modified host cell to produce GPP or geraniol, and expressing the polypeptide, (c) reducing the GPP or geraniol, and (d) recovering the reduced GPP or geraniol from the genetically modified host cell; wherein the genetically modified host cell is a yeast or bacterium.

2. The method of claim 1, wherein the polypeptide comprises an amino acid sequence having at least 99% identity to one of SEQ ID NOs: 1-8.

3. The method of claim 2, wherein the polypeptide comprises SEQ ID NO:1, SEQ ID NO:2, SEQ ID NO:3, SEQ ID NO:4, SEQ ID NO: 5, SEQ ID NO:6, SEQ ID NO:7, or SEQ ID NO:8.

4. The method of claim 1, wherein the polypeptide comprises an amino acid sequence having at least 99% identity to SEQ ID NO:1.

5. The method of claim 1, wherein the genetically modified host cell is a yeast.

6. The method of claim 1, wherein the genetically modified host cell is an *Escherichia, Enterobacter, Azotobacter, Erwinia, Bacillus, Pseudomonas, Klebsiella, Proteus, Salmonella, Serratia, Shigella, Rhizobia, Vitreoscilla*, and *Paracoccus* bacterium.

7. The method of claim 1, wherein the (b) culturing step comprises the genetically modified host cell producing GPP.

8. The method of claim 1, wherein the (b) culturing step comprises the genetically modified host cell producing geraniol.

* * * * *

SEQUENCE LISTING

<160> NUMBER OF SEQ ID NOS: 12

<210> SEQ ID NO 1
<211> LENGTH: 452
<212> TYPE: PRT
<213> ORGANISM: Sulfolobus acidocaldarius

<400> SEQUENCE: 1

Met Lys Glu Leu Lys Tyr Asp Val Leu Ile Ile Gly Gly Gly Phe Ala
1               5                   10                  15

Gly Ser Ser Ala Ala Tyr Gln Leu Ser Arg Arg Gly Leu Lys Ile Leu
            20                  25                  30

Leu Val Asp Ser Lys Pro Trp Asn Arg Ile Gly Asp Lys Pro Cys Gly
        35                  40                  45

Asp Ala Val Ser Lys Ala His Phe Asp Lys Leu Gly Met Pro Tyr Pro
    50                  55                  60

```
Lys Gly Glu Glu Leu Glu Asn Lys Ile Asn Gly Ile Lys Leu Tyr Ser
 65                  70                  75                  80

Pro Asp Met Gln Thr Val Trp Thr Val Asn Gly Gly Phe Glu Leu
             85                  90                  95

Asn Ala Pro Leu Tyr Asn Gln Arg Val Leu Lys Glu Ala Gln Asp Arg
             100                 105                 110

Gly Val Glu Ile Trp Asp Leu Thr Thr Ala Met Lys Pro Ile Phe Glu
             115                 120                 125

Asp Gly Tyr Val Lys Gly Ala Val Leu Phe Asn Arg Arg Thr Asn Glu
130                 135                 140

Glu Leu Thr Val Tyr Ser Lys Val Val Glu Ala Thr Gly Tyr Ser
145                 150                 155                 160

Arg Ser Phe Arg Ser Lys Leu Pro Pro Glu Leu Pro Ile Thr Glu Asp
                165                 170                 175

Leu Asp Asp Lys Asp Ala Asp Val Ala Tyr Arg Glu Val Leu Leu Thr
                180                 185                 190

Lys Glu Asp Ile Glu Asp His Asp Tyr Leu Arg Ile Phe Ile Asp Gln
                195                 200                 205

Glu Thr Ser Pro Gly Gly Tyr Trp Trp Tyr Phe Pro Lys Gly Lys Asn
210                 215                 220

Lys Val Asn Val Gly Leu Gly Ile Gln Gly Gly Met Gly Tyr Pro Ser
225                 230                 235                 240

Ile His Glu Tyr Tyr Lys Lys Tyr Leu Asp Lys Tyr Ala Pro Asp Val
                245                 250                 255

Asp Lys Ser Lys Leu Leu Val Lys Gly Gly Ala Leu Val Pro Thr Arg
                260                 265                 270

Arg Pro Leu Tyr Thr Met Ala Trp Asn Gly Ile Val Ile Gly Asp
                275                 280                 285

Ser Gly Phe Thr Val Asn Pro Val His Gly Gly Lys Gly Ser Ala
290                 295                 300

Met Ile Ser Gly Tyr Cys Ala Ala Lys Ala Ile Leu Ser Ala Phe Glu
305                 310                 315                 320

Thr Gly Asp Phe Ser Ala Ser Gly Leu Trp Asp Met Asn Ile Cys Tyr
                325                 330                 335

Val Asn Glu Tyr Gly Ala Lys Gln Ala Ser Leu Asp Ile Phe Arg Arg
                340                 345                 350

Phe Leu Gln Lys Leu Ser Asn Asp Asp Ile Asn Tyr Gly Met Lys Lys
                355                 360                 365

Lys Ile Ile Lys Glu Glu Asp Leu Leu Glu Ala Ser Glu Lys Gly Asp
                370                 375                 380

Leu His Leu Ser Val Ala Asp Lys Ala Met Arg Val Ile Ser Gly Leu
385                 390                 395                 400

Gly Arg Pro Ser Leu Leu Phe Lys Leu Lys Ala Val Ala Glu Ser Met
                405                 410                 415

Lys Lys Ile Lys Glu Leu Tyr Leu Asn Tyr Pro Arg Ser Pro Ser Ser
                420                 425                 430

Leu Gly Ser Trp Arg Arg Glu Val Asp Asn Val Leu Thr Glu Phe Asn
                435                 440                 445

Lys Ser Leu Ser
            450

<210> SEQ ID NO 2
<211> LENGTH: 317
```

```
<212> TYPE: PRT
<213> ORGANISM: Archaeoglobus fulgidus

<400> SEQUENCE: 2

Met Leu Lys Glu Glu Ile Ala Lys Arg Ala Glu Ile Ile Asn Lys Ala
1               5                   10                  15

Ile Glu Glu Leu Leu Pro Glu Arg Glu Pro Ile Gly Leu Tyr Lys Ala
            20                  25                  30

Ala Arg His Leu Ile Lys Ala Gly Gly Lys Arg Leu Arg Pro Val Ile
        35                  40                  45

Ser Leu Leu Ala Val Glu Ala Leu Gly Lys Asp Tyr Arg Lys Ile Ile
50                  55                  60

Pro Ala Ala Val Ser Ile Glu Thr Ile His Asn Phe Thr Leu Val His
65                  70                  75                  80

Asp Asp Ile Met Asp Arg Asp Glu Met Arg Arg Gly Val Pro Thr Val
                85                  90                  95

His Arg Val Tyr Gly Glu Ala Thr Ala Ile Leu Ala Gly Asp Thr Leu
            100                 105                 110

Phe Ala Glu Ala Phe Lys Leu Leu Thr Lys Cys Asp Val Glu Ser Glu
        115                 120                 125

Gly Ile Arg Lys Ala Thr Glu Met Leu Ser Asp Val Cys Ile Lys Ile
130                 135                 140

Cys Glu Gly Gln Tyr Tyr Asp Met Ser Phe Glu Lys Lys Glu Ser Val
145                 150                 155                 160

Ser Glu Glu Glu Tyr Leu Arg Met Val Glu Leu Lys Thr Gly Val Leu
                165                 170                 175

Ile Ala Ala Ser Ala Ala Leu Pro Ala Val Leu Phe Gly Glu Ser Glu
            180                 185                 190

Glu Ile Val Lys Ala Leu Trp Asp Tyr Gly Val Leu Ser Gly Ile Gly
        195                 200                 205

Phe Gln Ile Gln Asp Asp Leu Leu Asp Leu Thr Glu Glu Thr Gly Lys
210                 215                 220

Asp Trp Gly Ser Asp Leu Leu Lys Gly Lys Lys Thr Leu Ile Val Ile
225                 230                 235                 240

Lys Ala Phe Glu Lys Gly Val Lys Leu Lys Thr Phe Gly Lys Glu Lys
                245                 250                 255

Ala Asp Val Ser Glu Ile Arg Asp Asp Ile Glu Lys Leu Arg Glu Cys
            260                 265                 270

Gly Ala Ile Asp Tyr Ala Ala Ser Met Ala Arg Lys Met Ala Glu Glu
        275                 280                 285

Ala Lys Arg Lys Leu Glu Val Leu Pro Glu Ser Lys Ala Lys Glu Thr
290                 295                 300

Leu Leu Glu Leu Thr Asp Phe Leu Val Thr Arg Lys Lys
305                 310                 315

<210> SEQ ID NO 3
<211> LENGTH: 266
<212> TYPE: PRT
<213> ORGANISM: Methanocaldococcus infernus

<400> SEQUENCE: 3

Met Leu Lys Lys Leu Ile Leu Lys Gly Tyr Lys Phe Thr Asn Asn Phe
1               5                   10                  15

Ile Gly Phe Lys Ile Tyr Glu Lys Leu Leu Glu Met Glu Ile Asp Lys
            20                  25                  30
```

-continued

```
Asn Lys Ile Pro Lys His Ile Gly Ile Ile Met Asp Gly Asn Arg Arg
         35                  40                  45

Leu Gly Gln Ile Leu Gly Asn Lys Ile Glu Gly His Lys Leu Gly Ala
 50                  55                  60

Lys Lys Val Lys Glu Val Leu Arg Trp Cys Leu Glu Leu Gly Val Lys
 65                  70                  75                  80

Val Val Thr Leu Tyr Ser Phe Ser Ile Glu Asn Phe Asn Arg Pro Lys
                     85                  90                  95

Asp Glu Val Glu Ala Leu Met Asn Leu Phe Lys Glu Lys Phe Tyr Glu
                100                 105                 110

Ala Ala Glu Asn Arg Asp Ile His Lys Tyr Lys Val Arg Ile Lys Ala
            115                 120                 125

Ile Gly Arg Leu Asp Leu Leu Pro Glu Asp Val Arg Glu Ala Ile Arg
        130                 135                 140

Tyr Ala Glu Glu Lys Thr Lys His Tyr Ser Asn Tyr Ile Asn Val
145                 150                 155                 160

Ala Ile Ala Tyr Gly Gly Gln Gln Glu Ile Val Asp Ala Val Arg Lys
                    165                 170                 175

Ile Ala Glu Lys Val Lys Arg Gly Glu Ile Pro Glu Glu Ile Asn
                180                 185                 190

Lys Glu Leu Ile Asp Lys His Leu Tyr Thr Ala His Leu Pro Tyr Pro
            195                 200                 205

Tyr Pro Asp Leu Ile Ile Arg Thr Ser Gly Glu Glu Arg Ile Ser Asn
        210                 215                 220

Phe Leu Ile Trp Gln Ser Ser Tyr Ser Glu Leu Tyr Phe Cys Asp Val
225                 230                 235                 240

Tyr Trp Pro Leu Phe Arg Arg Ile Asp Leu Leu Arg Ala Ile Arg Glu
                    245                 250                 255

Tyr Gln Arg Arg Glu Arg Arg Phe Gly Arg
                260                 265

<210> SEQ ID NO 4
<211> LENGTH: 450
<212> TYPE: PRT
<213> ORGANISM: Pyrolobus fumarius

<400> SEQUENCE: 4

Met Thr Arg Glu Cys Arg Phe Glu Val Leu Ile Ala Gly Gly Gly Pro
  1               5                  10                  15

Ala Gly Thr Val Ala Ala Tyr His Leu Ala Arg Met Gly Phe Asn Val
                20                  25                  30

Ala Leu Phe Glu Ile Arg Gly Trp Asp Asn Val Trp Gly Lys Pro Cys
            35                  40                  45

Gly Asp Ala Ile Gly Ala His His Phe Pro Asn Ala Gly Leu Pro Glu
        50                  55                  60

Pro Pro Ser Glu Val Ile His Asn Lys Ile Asp Gly Val Leu Ile Tyr
 65                  70                  75                  80

Ser Pro Ser Leu Glu Thr Val Tyr Arg Val Arg Gly Glu Gly Tyr Ile
                    85                  90                  95

Ile Asp Arg Arg Gly Leu Gly Arg Trp Leu Leu Arg Glu Ala Glu Arg
                100                 105                 110

Arg Gly Ala Gln Ile Phe Leu Glu Ser Ser Val Glu Ala Pro Ile Val
            115                 120                 125

Glu Asn Gly Arg Val Ala Gly Leu Arg Val Arg Leu Lys Ser Gly Glu
        130                 135                 140
```

His Leu Glu Cys Arg Gly Asn Ile Val Ile Glu Ala Thr Gly Tyr Ser
145                 150                 155                 160

Met Val Val Lys Arg Gly Leu Pro Arg Asp Trp Pro Val Ala Glu Arg
                165                 170                 175

Leu Asp Met Lys Asp Thr Asn Ile Ala Tyr Arg Glu Val Gln Glu Leu
            180                 185                 190

Ser Asp Glu Val Glu Pro Asn Tyr Ile Arg Ile Tyr Ile Asn Gln
        195                 200                 205

Glu Ile Ala Pro Gly Gly Tyr Trp Trp Leu Phe Pro Glu Gly Lys Asn
    210                 215                 220

Val Ile Asn Ile Gly Leu Gly Val Gln Gly Val Gly Asn Pro His
225                 230                 235                 240

Pro Arg Gln Gln Phe Thr Gln Leu Tyr Glu Arg Gly Leu Ala Pro Pro
                245                 250                 255

Pro Arg Arg Val Ile Glu Ala Gly Ala Val Val Pro Thr Arg Arg
        260                 265                 270

Pro Ala Asp Thr Leu Val Gly Pro Gly Leu Leu Val Ile Gly Asp Ala
            275                 280                 285

Gly Phe Thr Val Asn Pro Val His Gly Gly Ile Gly Tyr Ala Phe
    290                 295                 300

Tyr Ala Ala Arg Leu Ala Ala Glu Ala Tyr Lys Glu Ala His Asp Lys
305                 310                 315                 320

Gly Cys Phe Ser Glu Glu Cys Leu Trp Ser Leu Asn Thr Arg Tyr Met
                325                 330                 335

Lys Ser Leu Gly Ala Lys Gln Ala Ala Leu Asp Ile Phe Arg Leu Phe
            340                 345                 350

Leu Gln Arg Leu Ser Asn Asp Asp Ile Glu Tyr Gly Met Ser Gln Arg
        355                 360                 365

Ile Met Pro Glu Ser Asp Val Tyr Phe Thr Ser Thr Thr Gly Glu Leu
    370                 375                 380

Arg Leu Ser Val Val Glu Lys Ala Met Ile Ile Leu Arg Gly Leu Arg
385                 390                 395                 400

Arg Pro Ser Leu Leu Leu Lys Leu Lys Leu Val Ala Glu Tyr Met Glu
                405                 410                 415

Lys Val Arg Lys Leu Tyr His Ala Tyr Pro Glu Asp Pro Arg Lys Leu
            420                 425                 430

Ala Gln Trp Arg Glu Gln Val Lys Ser Leu Phe Asn Glu Phe Leu Val
        435                 440                 445

Lys Ile
    450

<210> SEQ ID NO 5
<211> LENGTH: 392
<212> TYPE: PRT
<213> ORGANISM: Streptomyces coelicolor

<400> SEQUENCE: 5

Met Arg Thr Thr Glu Ser Glu Lys Gly Leu Arg Met Pro Gly Leu Pro
1               5                   10                  15

Pro Met Val Ala Pro Ala Glu Gln Val Asp Asp Pro Val Thr Ala
                20                  25                  30

Thr Asp Ala Ala Asn Ala Val Asp Ala Val Leu Arg Gly Val Leu Asp
            35                  40                  45

Glu Arg Leu Arg His Cys Arg Ala Val Asp Pro Leu Phe Ala Arg Glu

```
                    50                  55                  60
Leu Ala Asp Arg Leu Ala Ala Leu Thr Ala Arg Gly Gly Lys Arg Leu
 65                  70                  75                  80

Arg Thr Ala Phe Ala His Cys Gly Trp Arg Ala Ala Gly Gly Ser Gly
                     85                  90                  95

Asp Ala Thr Ala Val Leu Arg Thr Gly Ala Ala Leu Glu Leu Leu Gln
                    100                 105                 110

Ala Cys Ala Leu Val His Asp Asp Val Met Asp Gly Ser Val Gln Arg
                115                 120                 125

Arg Gly Ala Pro Ala Leu His Val Asp Leu Ala Arg Gly His Trp Ala
            130                 135                 140

Ala Gly Met His Gly Ser Ser Glu Ser Phe Gly Thr Ser Ala Ala Val
145                 150                 155                 160

Leu Thr Gly Asp Leu Ala Leu Ala Trp Ala Asp Leu Leu Thr Glu
                165                 170                 175

Thr Ala Leu Gly Thr Pro His Gly Pro Arg Leu His Gly Glu Trp Arg
                180                 185                 190

Ala Met Arg Thr Glu Met Val Ala Gly Gln Tyr Arg Asp Leu His Ala
                195                 200                 205

Gln Ala Ala Arg Ser Ser Gly Val Asp Glu Ala Leu Ala Ile Ala Thr
210                 215                 220

Leu Lys Ser Ala Leu Tyr Thr Val Ala Arg Pro Leu Ala Leu Gly Ala
225                 230                 235                 240

Val Leu Ala Gly Ala Ala Asp Gly Asp Ala Leu Glu Ala Leu Arg Ala
                245                 250                 255

Ala Gly Arg Cys Ala Gly Leu Ala Phe Gln Leu Arg Asp Asp Leu Leu
                260                 265                 270

Gly Ala Phe Gly Asp Pro Ala Leu Thr Gly Lys Pro Ala Asp Asp
                275                 280                 285

Leu Arg Ser Arg Lys Leu Thr Tyr Leu Leu Ala Val Ala Val Arg Leu
                290                 295                 300

Ala Asp Ala Ala Asp Asp His Leu Ala Ala Ala Leu Ala Pro Asp
305                 310                 315                 320

Ala Asp Pro Lys Ser Glu Lys Ala Val Arg Gln Val Arg Ser Ala Leu
                325                 330                 335

Val Arg Thr Gly Ala Arg Asp Leu Val Glu Thr Lys Ile Gly Glu Leu
                340                 345                 350

Thr Asp Met Ser Leu Ala His Phe Asp Arg Cys Gly Ala Arg Pro Ala
                355                 360                 365

Val Arg His Glu Phe Ala Leu Ile Gly Arg Ala Thr Gly Ala Val
                370                 375                 380

Pro Arg Gly Thr Gly Glu Val Val
385                 390

<210> SEQ ID NO 6
<211> LENGTH: 277
<212> TYPE: PRT
<213> ORGANISM: Thermococcus nautili

<400> SEQUENCE: 6

Met Glu Ala Arg Ala Phe Ile Glu Ile Thr Arg Pro His Asn Cys Val
 1               5                  10                  15

Leu Ala Gly Val Val Gly Leu Leu Gly Ser Ile Val Ala Val Gly His
                20                  25                  30
```

```
Phe Pro Glu Pro Val Lys Ala Leu Leu Val Phe Leu Val Val Thr Leu
        35                  40                  45

Gly Cys Ser Ala Gly Asn Thr Ile Asn Asp Tyr Phe Asp Tyr Glu Ile
 50                  55                  60

Asp Arg Ile Asn Arg Pro Glu Arg Pro Leu Pro Arg Gly Ala Met Ser
 65                  70                  75                  80

Arg Lys Thr Ala Phe Trp Tyr Ala Met Ala Leu Phe Ala Ile Gly Leu
                 85                  90                  95

Ile Leu Ala Ser Leu Ile Asn Val Tyr Ala Phe Leu Leu Ala Val Val
            100                 105                 110

Ala Tyr Thr Thr Met Phe Leu Tyr Ala Trp Lys Leu Lys Pro Leu Pro
            115                 120                 125

Phe Val Gly Asn Leu Val Val Ala Gly Leu Thr Gly Ala Thr Pro Leu
        130                 135                 140

Tyr Gly Ala Ile Ala Val Gly Lys Ile Gly Leu Ala Gly Tyr Leu Ala
145                 150                 155                 160

Leu Cys Ala Phe Leu Val Asn Val Ala Arg Glu Val Ile Lys Asp Ile
                165                 170                 175

Glu Asp Val Glu Gly Asp Leu Ala Lys Gly Ala Arg Thr Leu Pro Ile
            180                 185                 190

Val Ile Gly Lys Lys Ser Ala Tyr Val Gly Ala Phe Phe Ala Val
        195                 200                 205

Leu Thr Val Ile Ala Ser Phe Leu Pro Ile Lys Ala Gly Val Gly Leu
        210                 215                 220

Ser Tyr Leu Ala Met Val Pro Val Asp Ala Ile Ile Leu Tyr Ser Ala
225                 230                 235                 240

Phe Leu Ile Leu Arg Ser Gln Asp Arg Glu Thr Ala His Arg Ser Gln
                245                 250                 255

Lys Leu Leu Lys Ile Ser Ile Phe Leu Ala Val Met Ala Phe Met Ile
            260                 265                 270

Ala Ser Leu Val Arg
            275

<210> SEQ ID NO 7
<211> LENGTH: 354
<212> TYPE: PRT
<213> ORGANISM: Thermoplasma acidophilum

<400> SEQUENCE: 7

Met Gln Ile Glu Thr Glu Asp Pro His Glu Thr Ile Asn Asn Tyr Lys
 1               5                  10                  15

Leu Arg Ile Asp Glu Arg Ile Ser Arg Phe Phe Asp Arg Lys Glu Ala
             20                  25                  30

Glu Thr Lys Asp Asp Leu Ser Arg Arg Val Ile Arg Met Ile Arg Glu
         35                  40                  45

Tyr Thr Glu Gly Gly Gly Lys Arg Leu Arg Pro Ile Phe Leu Val Leu
     50                  55                  60

Gly Tyr Arg Leu Phe Ala Asp Glu Asn Asn Ala Ile Phe Asp Ala Ser
 65                  70                  75                  80

Ile Ser Ile Glu Leu Ala Gln Ser Tyr Leu Leu Ile His Asp Asp Val
                 85                  90                  95

Ile Asp Asp Ser Asp Leu Arg Arg Gly Lys Pro Ser Met His Ile Arg
            100                 105                 110

Leu Trp Arg Ser Phe Phe Pro Glu Ser Glu Lys Gly Lys Lys Met Gly
        115                 120                 125
```

Glu Gly Leu Ala Ile Val Ala Gly Asp Leu Ala Glu Thr Tyr Ala His
    130                 135                 140

Glu Ser Leu Ile Asn Ser Asp Phe Asp Pro Ser Leu Leu Leu Leu Ala
145                 150                 155                 160

Asp Met Glu Leu Thr Lys Thr Ile Glu Met Thr Gly Tyr Gly Gln Phe
                165                 170                 175

Leu Asp Val Val Ser Gly Thr Leu Asn Asp Phe Arg Glu Asn Asp Leu
            180                 185                 190

Ile Arg Leu His Leu Trp Lys Thr Ala Arg Tyr Thr Leu Glu Gly Pro
        195                 200                 205

Leu Ala Met Gly Ala Leu Leu Ser Gly Arg His Asp Gln Ile Met Asp
    210                 215                 220

Leu Arg Leu Phe Gly Arg Thr Leu Gly Ile Ala Phe Gln Leu Lys Asp
225                 230                 235                 240

Asp Ile Leu Gly Leu Phe Gly Asp Glu Ala Thr Thr Gly Lys Ser Ile
                245                 250                 255

Tyr Ser Asp Val Asn Glu Gly Lys Arg Thr Leu Leu Met Ile Lys Ala
            260                 265                 270

Met Glu Phe Ser Asp Arg Gln Asp Ala Glu Phe Ile Asp Arg Ile Leu
        275                 280                 285

Arg Arg Gly Asn Val Thr Gln Glu Glu Phe Glu Arg Ile Arg Asn Ile
    290                 295                 300

Val Met Lys Ser Gly Ser Tyr Asp Tyr Ser Val Lys Leu Met Asp Ser
305                 310                 315                 320

Leu Val Ala Lys Ser Lys Glu Tyr Leu Asn Arg Ile Arg Gly Asn Ser
                325                 330                 335

Cys Ala Lys Thr Tyr Leu Ser Trp Leu Ser Asp Tyr Leu Val Ala Arg
            340                 345                 350

Asp His

<210> SEQ ID NO 8
<211> LENGTH: 389
<212> TYPE: PRT
<213> ORGANISM: Methanosarcina acetivorans

<400> SEQUENCE: 8

Met Tyr Asp Leu Ile Ile Val Gly Gly Pro Ser Gly Ala Ser Ala
1               5                   10                  15

Gly Arg Val Ala Gly Ser Ala Gly Ile Ser Thr Leu Leu Glu Lys
            20                  25                  30

Glu Asn Phe Pro Arg Tyr Lys Pro Cys Gly Ala Leu Ser Pro Tyr
        35                  40                  45

Ala Leu Ser Cys Leu Asp Phe Glu Leu Pro Glu Ser Val Val Glu Arg
    50                  55                  60

Asp Ile Ser Lys Val Arg Val His Phe Arg Glu Leu Cys Leu Glu Arg
65                  70                  75                  80

Gln Arg Asp Tyr Arg Leu Ala Leu Leu Val Ser Arg Lys Ala Phe Asp
                85                  90                  95

Asn Leu Leu Leu Asp Lys Ala Arg Glu Thr Gly Ile Glu Val His Cys
            100                 105                 110

Gly Glu Lys Val Leu Asp Cys Glu Glu Gly Glu Glu Trp Val Glu Val
        115                 120                 125

Arg Thr Ser Arg Asn Ser Tyr Leu Ala Lys Phe Val Leu Ile Ala Glu
    130                 135                 140

```
Gly Ser Glu Gly Ile Leu Lys Tyr Lys Val Arg Pro Gln Arg Ala Arg
145                 150                 155                 160

Arg Thr Glu Tyr Asp Leu Ala Leu Val Ser Glu Ile Pro Glu Glu Asp
                165                 170                 175

Glu Val Ile Arg Asn Arg Phe Pro Gly Met Val Asp Ile His Phe Gly
            180                 185                 190

Val Ala Pro Gly Gly Tyr Gly Trp Val Phe Pro His Ala Gly Tyr Tyr
        195                 200                 205

Ser Val Gly Val Val Gly Thr Ala Glu His Leu Lys His Pro Lys Lys
    210                 215                 220

Val Met Gln Asp Phe Leu Gln Ala Asn Asp Phe Ser Gly Glu Phe Gln
225                 230                 235                 240

Val Cys Ser His Ile Ile Pro Val Gly Gly Ile Lys Arg Lys Thr Val
                245                 250                 255

Ser Ser Arg Ile Leu Leu Ser Gly Asp Ala Ala Gly Phe Val Asp Ala
            260                 265                 270

Phe Ile Gly Glu Gly Ile Ala Tyr Ala Ile Arg Ser Gly Gln Leu Ala
        275                 280                 285

Ala Glu Ile Val Ala Asp Leu Val Leu Tyr Asn Arg Lys Leu Ser Asp
    290                 295                 300

Leu Lys Glu Tyr Glu Ser Arg Cys Gly Gln Glu Phe Gly Asn Phe Leu
305                 310                 315                 320

Val Ser Ser Leu Lys Leu Glu Lys Val Met His Arg Phe Pro Glu Thr
                325                 330                 335

Ser Phe Lys Leu Ala Leu Ser Arg Glu Ile Leu Asp Lys Tyr Leu
            340                 345                 350

Asp Glu Val Val Ile Asn Arg Ser His Lys Asp Tyr Val Arg Trp Leu
    355                 360                 365

Leu Leu Asn Phe Ser Leu Ala Glu Pro Ala Ser Arg Ile Met Ser Met
370                 375                 380

Ala Gly Lys Asn Gln
385

<210> SEQ ID NO 9
<211> LENGTH: 16
<212> TYPE: PRT
<213> ORGANISM: Methanocaldococcus infernus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 9

Tyr Xaa Trp Xaa Phe Pro Xaa Xaa Xaa Xaa Xaa Xaa Xaa Gly Xaa Gly
1               5                   10                  15

<210> SEQ ID NO 10
<211> LENGTH: 36
```

```
<212> TYPE: DNA
<213> ORGANISM: Artificial Sequence
<220> FEATURE:
<223> OTHER INFORMATION: Forward primer for amplifying SaGGR from the
      pSKB3-SaGGR plasmid

<400> SEQUENCE: 10
gatatacata tgaaggaact taaatatgac gttctg                                36

<210> SEQ ID NO 11
<211> LENGTH: 45
<212> TYPE: DNA
<213> ORGANISM: Artificial Sequence
<220> FEATURE:
<223> OTHER INFORMATION: Reverse primer for amplifying SaGGR from the
      pSKB3-SaGGR plasmid

<400> SEQUENCE: 11
gtcgacggag ctcgaactta aactttgtt aaactctgtt agaac                       45

<210> SEQ ID NO 12
<211> LENGTH: 17
<212> TYPE: PRT
<213> ORGANISM: Sulfolobus acidocaldarius
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 12

Tyr Xaa Trp Xaa Phe Pro Xaa Xaa Xaa Xaa Xaa Xaa Xaa Xaa Gly Xaa
1               5                   10                  15

Gly
```